(12) United States Patent
Peliks

(10) Patent No.: US 10,278,678 B2
(45) Date of Patent: May 7, 2019

(54) TISSUE REMOVAL DEVICE AND METHOD OF USE

(71) Applicant: MERIT MEDICAL SYSTEMS, INC., South Jordan, UT (US)

(72) Inventor: Robert Bilgor Peliks, San Francisco, CA (US)

(73) Assignee: Merit Medical Systems, Inc., South Jordan, UT (US)

( * ) Notice: Subject to any disclaimer, the term of this patent is extended or adjusted under 35 U.S.C. 154(b) by 347 days.

(21) Appl. No.: 15/004,911

(22) Filed: Jan. 23, 2016

(65) Prior Publication Data

US 2016/0174949 A1    Jun. 23, 2016

Related U.S. Application Data

(63) Continuation of application No. 13/653,395, filed on Oct. 16, 2012, now Pat. No. 9,271,700, which is a continuation of application No. 13/452,863, filed on Apr. 21, 2012, now Pat. No. 8,317,727, which is a continuation-in-part of application No. PCT/US2011/061089, filed on Nov. 16, 2011, which is a continuation of application No. 61/415,850, filed on Nov. 21, 2010.

(51) Int. Cl.
*A61B 10/02* (2006.01)
*A61B 17/00* (2006.01)
*A61B 17/32* (2006.01)
*A61B 17/3207* (2006.01)

(52) U.S. Cl.
CPC ...... *A61B 10/0266* (2013.01); *A61B 10/0283* (2013.01); *A61B 17/32002* (2013.01); *A61B 17/320783* (2013.01); *A61B 2010/0208* (2013.01); *A61B 2017/00685* (2013.01)

(58) Field of Classification Search
CPC ............ A61B 10/0266; A61B 10/0283; A61B 17/32002; A61B 2010/0208; A61B 2017/00685; A61B 17/320783
See application file for complete search history.

(56) References Cited

U.S. PATENT DOCUMENTS

| | | |
|---|---|---|
| 3,732,858 A | 5/1973 | Banko |
| 4,099,518 A | 7/1978 | Baylis |
| 4,649,919 A | 3/1987 | Thimsen et al. |
| 5,488,958 A | 2/1996 | Topel et al. |
| 5,591,187 A | 1/1997 | Dekel |
| 5,762,069 A | 6/1998 | Kelleher et al. |
| 6,083,237 A | 7/2000 | Huitema et al. |
| 6,086,543 A | 7/2000 | Anderson et al. |
| 7,008,381 B2 * | 3/2006 | Janssens ............ A61B 10/0233 600/564 |

(Continued)

*Primary Examiner* — Sean P Dougherty
(74) *Attorney, Agent, or Firm* — Stoel Rives LLP

(57) ABSTRACT

A biopsy device for acquiring more than one tissue sample is disclosed. The biopsy device can have at least two tissue engaging elements, where at least one element contains a helical feature. A control mechanism can be used to spin an outer element relative to an internal element, resulting in transport of multiple tissue samples from the mass of tissue to an accessible collection chamber. The outer element may have a sharp distal end which may sever the samples from the mass of tissue. Samples may be stored sequentially in the collection chamber and be removed by the operator.

7 Claims, 14 Drawing Sheets

(56) References Cited

U.S. PATENT DOCUMENTS

| | | |
|---|---|---|
| 7,278,970 B2 | 10/2007 | Goldenberg |
| 7,338,456 B2 | 3/2008 | Goldenberg |
| 7,608,049 B2 | 10/2009 | Goldenberg |
| 7,635,340 B2 | 12/2009 | Vetter |
| 7,758,514 B2 | 7/2010 | Grigoryants |
| 7,806,871 B2 | 10/2010 | Li et al. |
| 8,444,573 B2 | 5/2013 | Flatland |
| 9,230,535 B2 | 4/2016 | Zaretzka |
| 2002/0131896 A1 | 9/2002 | Hunnell et al. |
| 2005/0209530 A1 | 9/2005 | Pflueger |
| 2006/0074343 A1 | 4/2006 | Hibner |
| 2008/0125856 A1 | 5/2008 | Perez-Cruet et al. |
| 2008/0234602 A1 | 9/2008 | Oostman et al. |
| 2008/0249553 A1 | 10/2008 | Gruber et al. |
| 2009/0198149 A1 | 8/2009 | Privetera et al. |
| 2009/0227893 A1 | 9/2009 | Coonahan et al. |
| 2011/0004120 A1 | 1/2011 | Drubetsky |
| 2011/0144533 A1 | 6/2011 | Chudzik |

\* cited by examiner

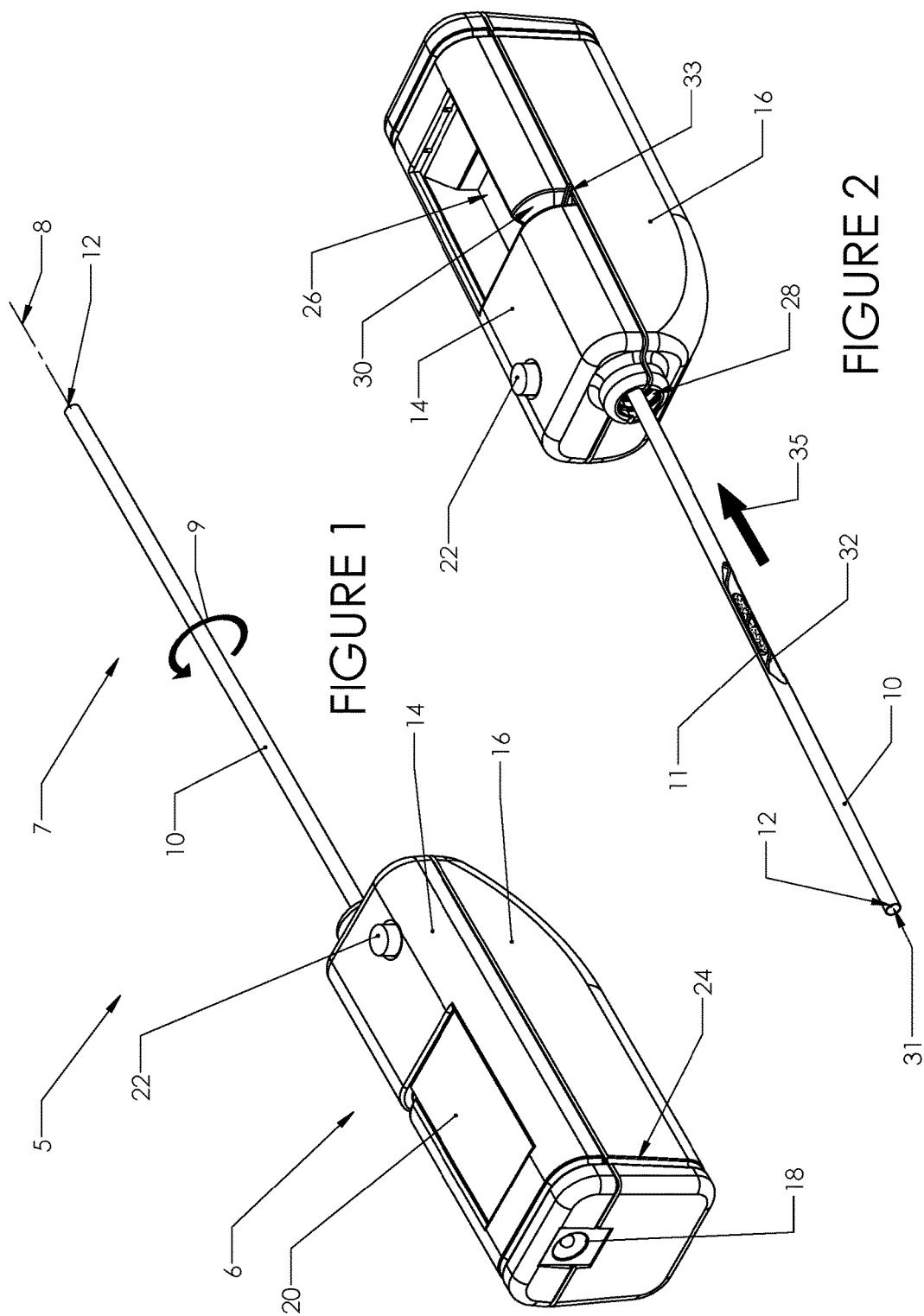

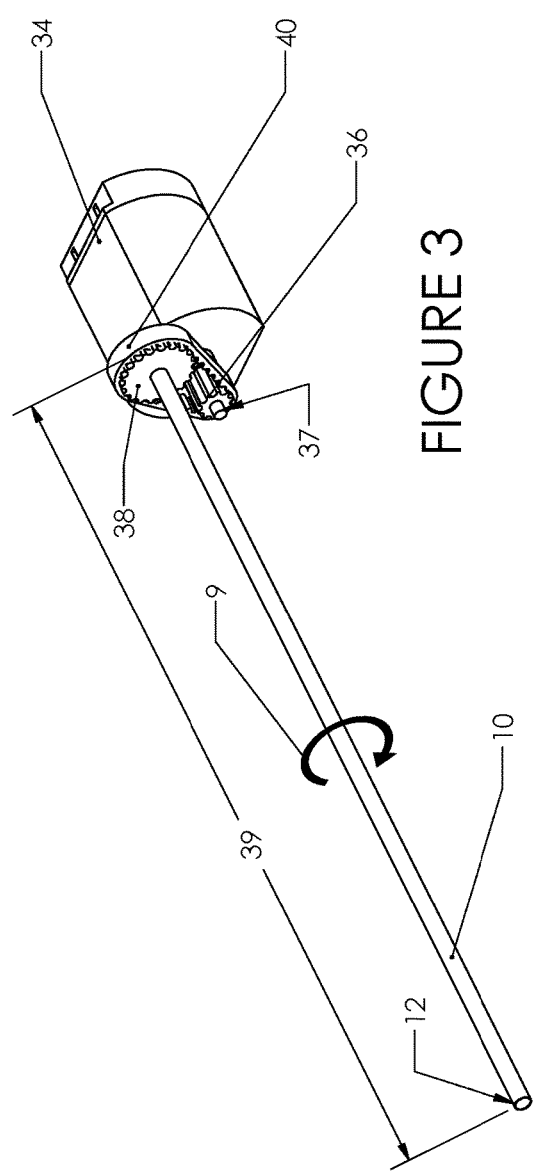
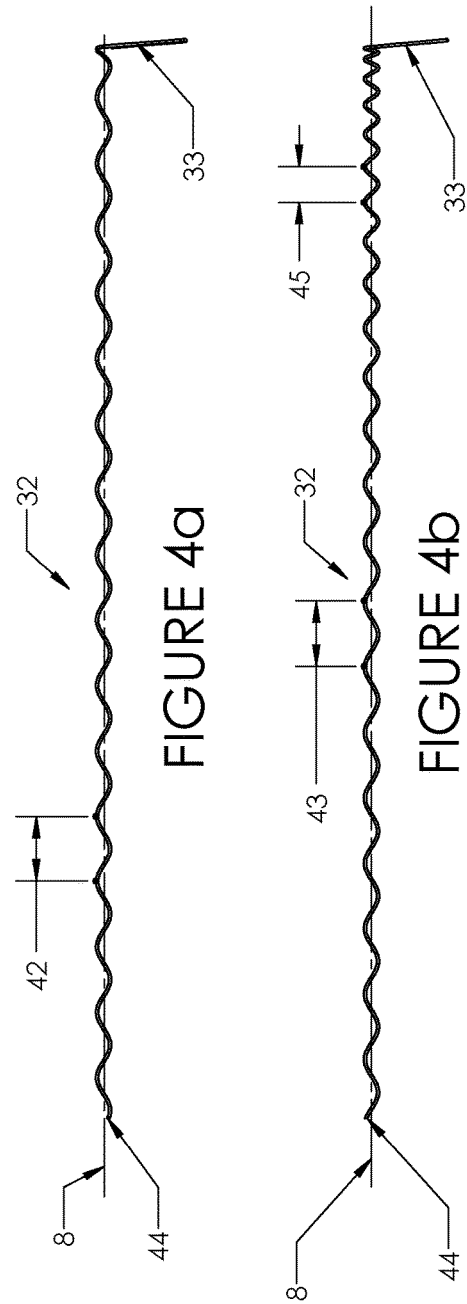
FIGURE 3
FIGURE 4a
FIGURE 4b

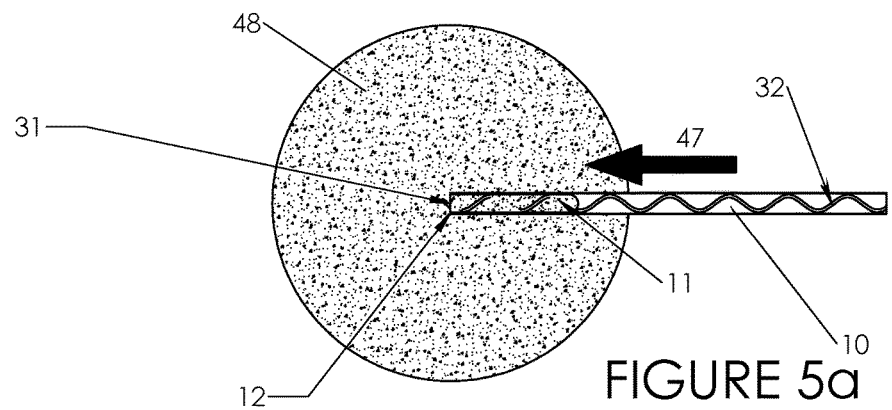
FIGURE 5a
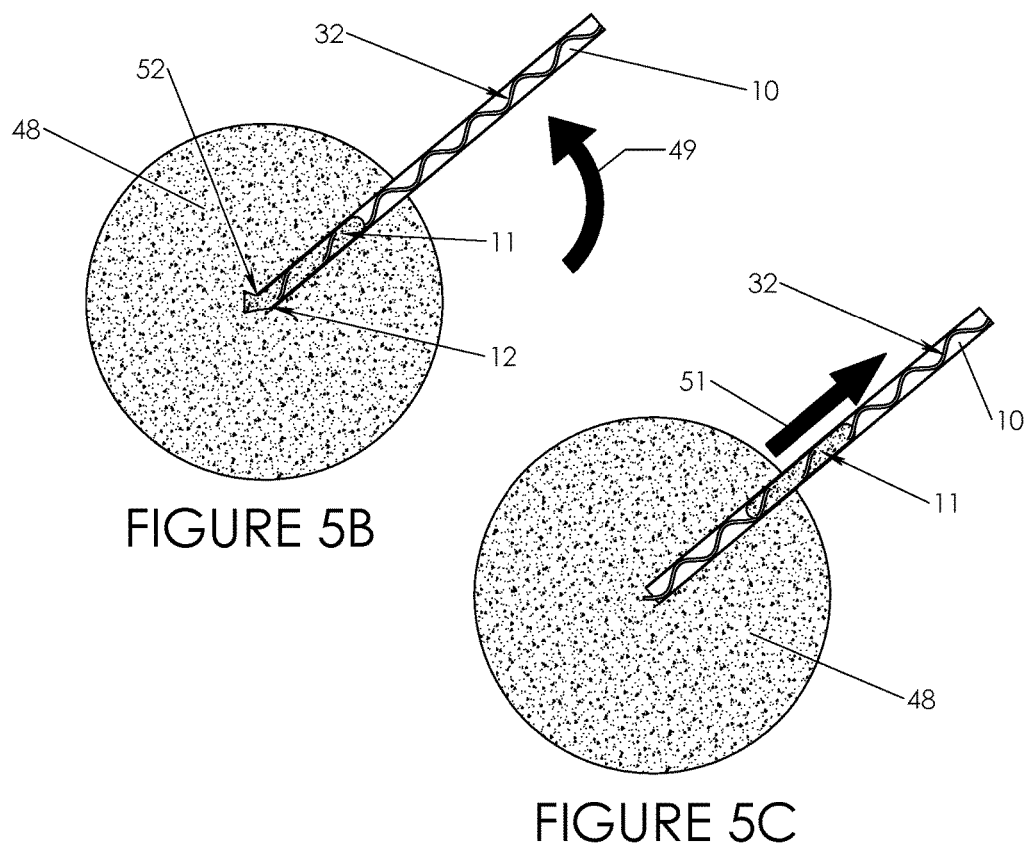
FIGURE 5B
FIGURE 5C

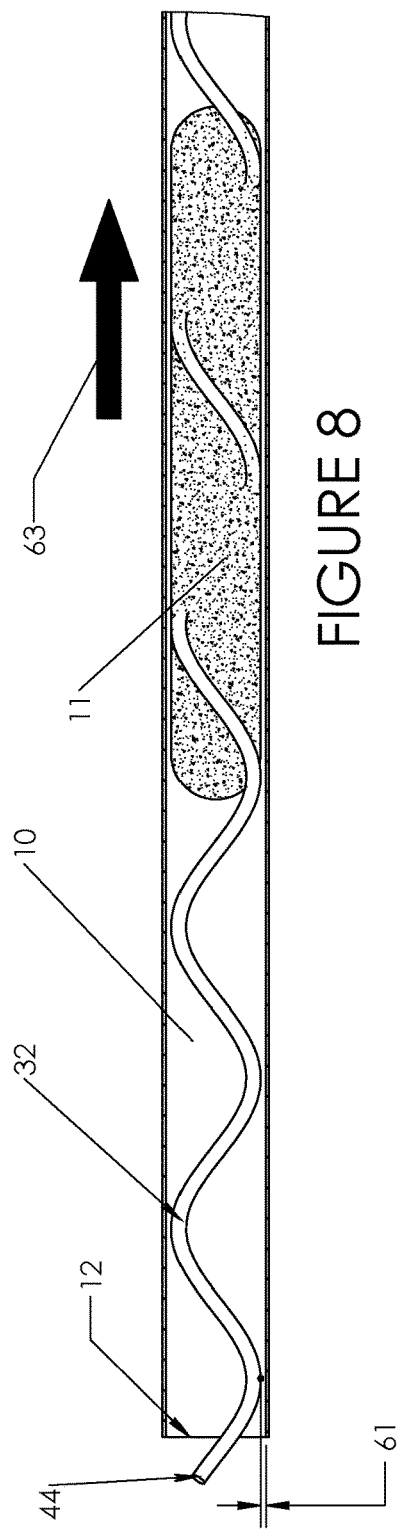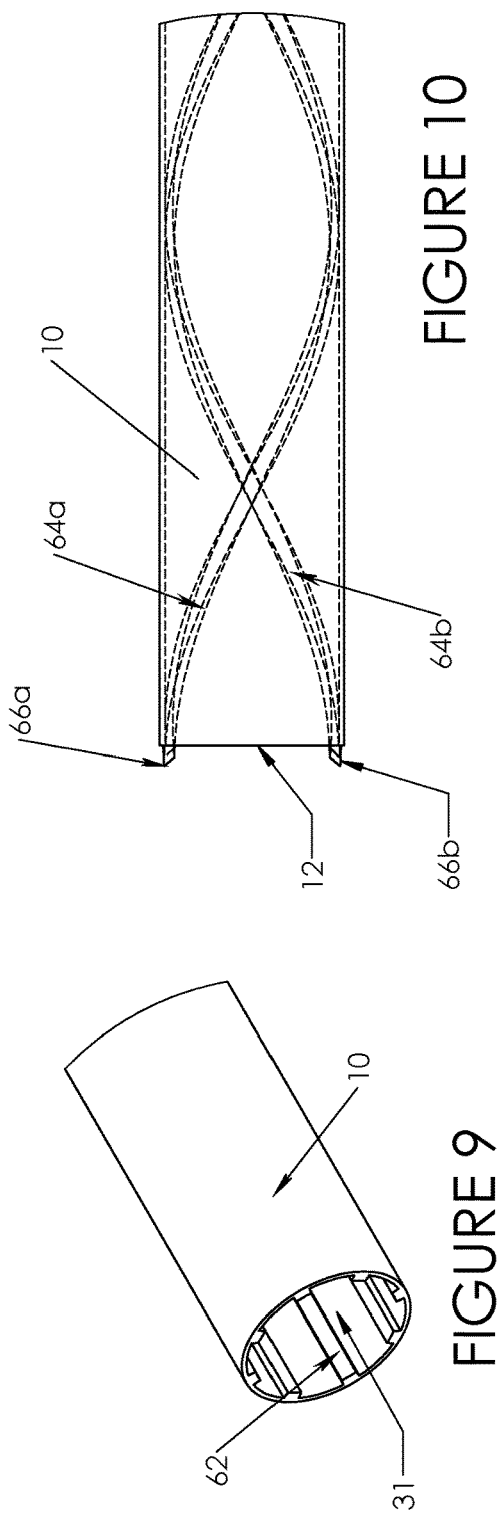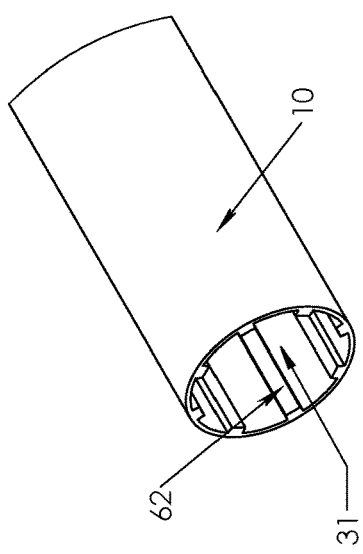

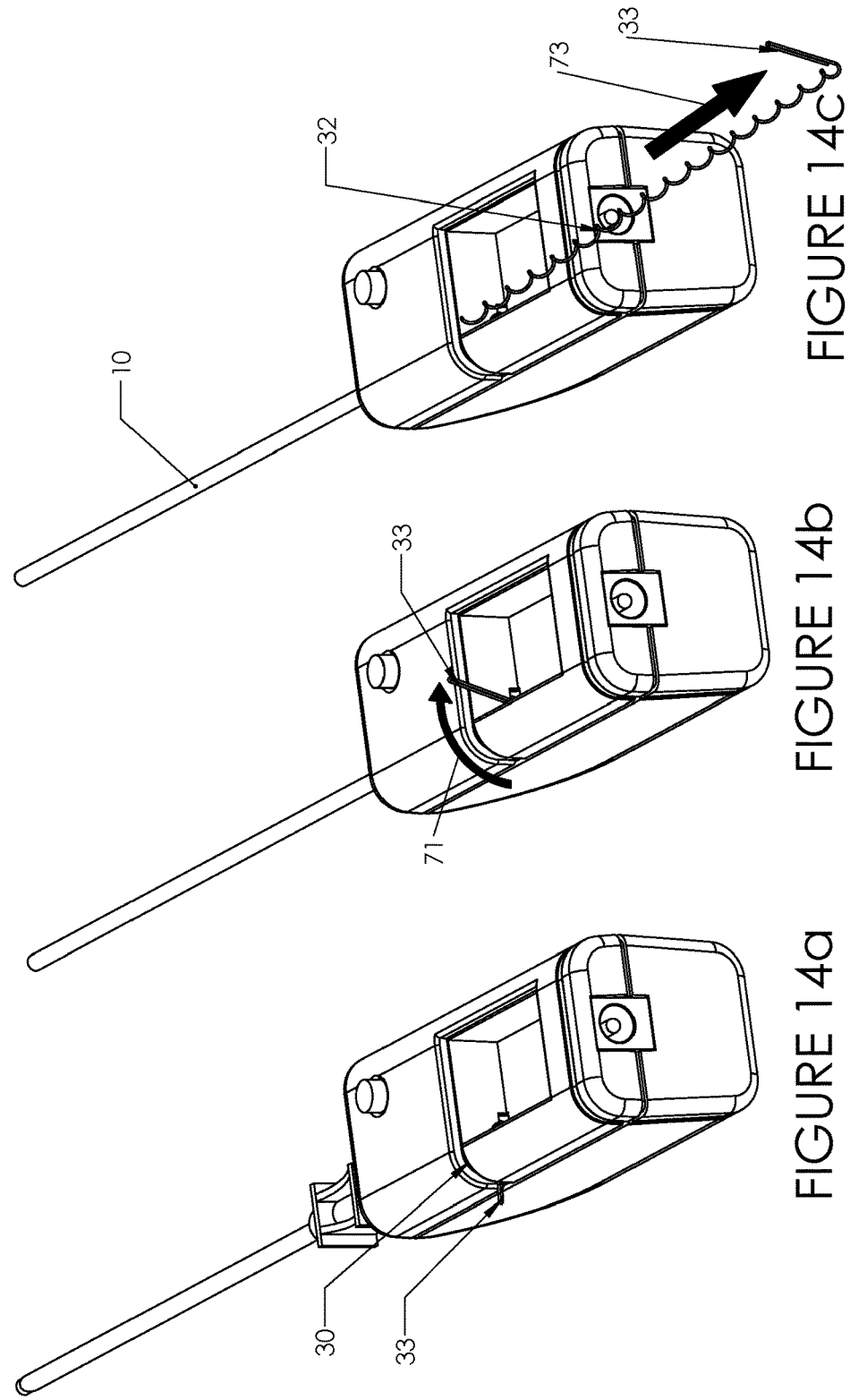

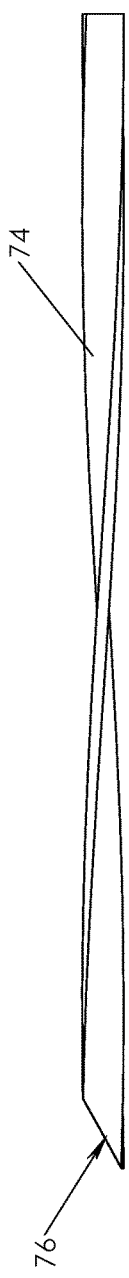
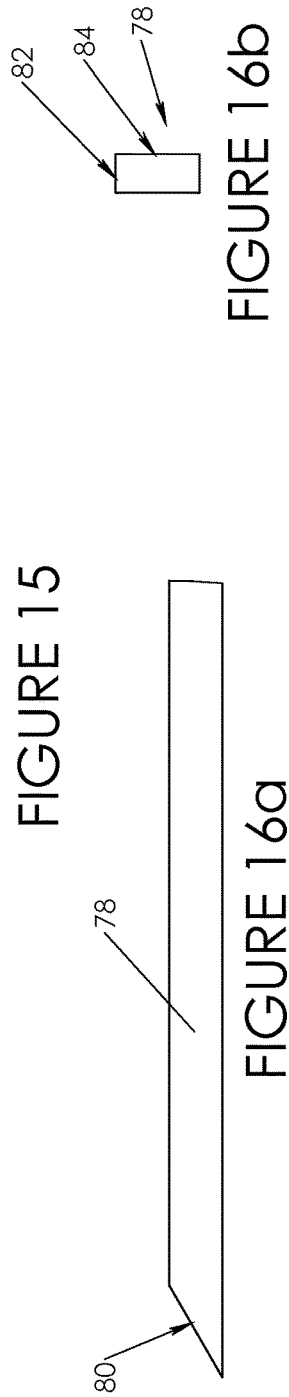
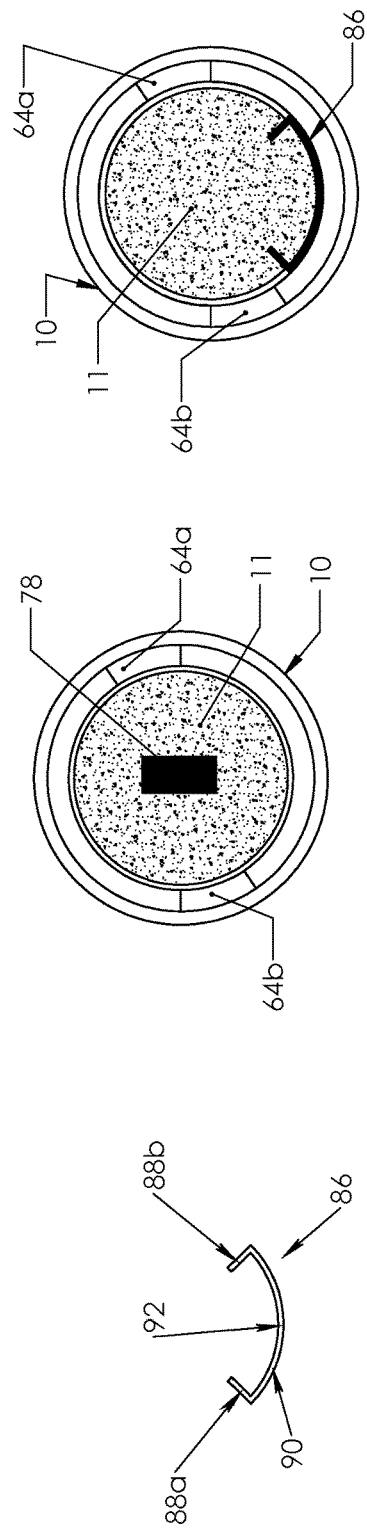

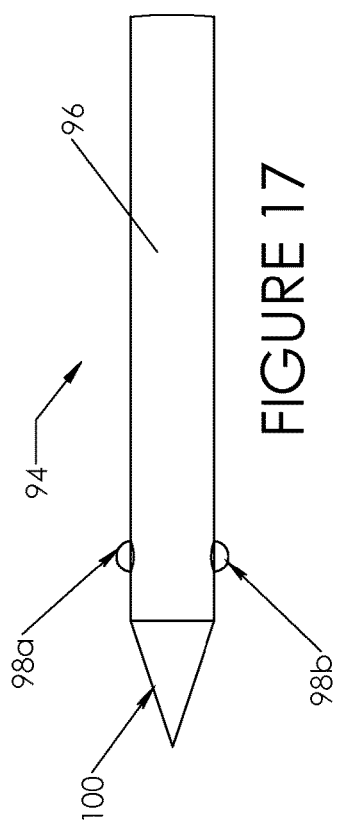
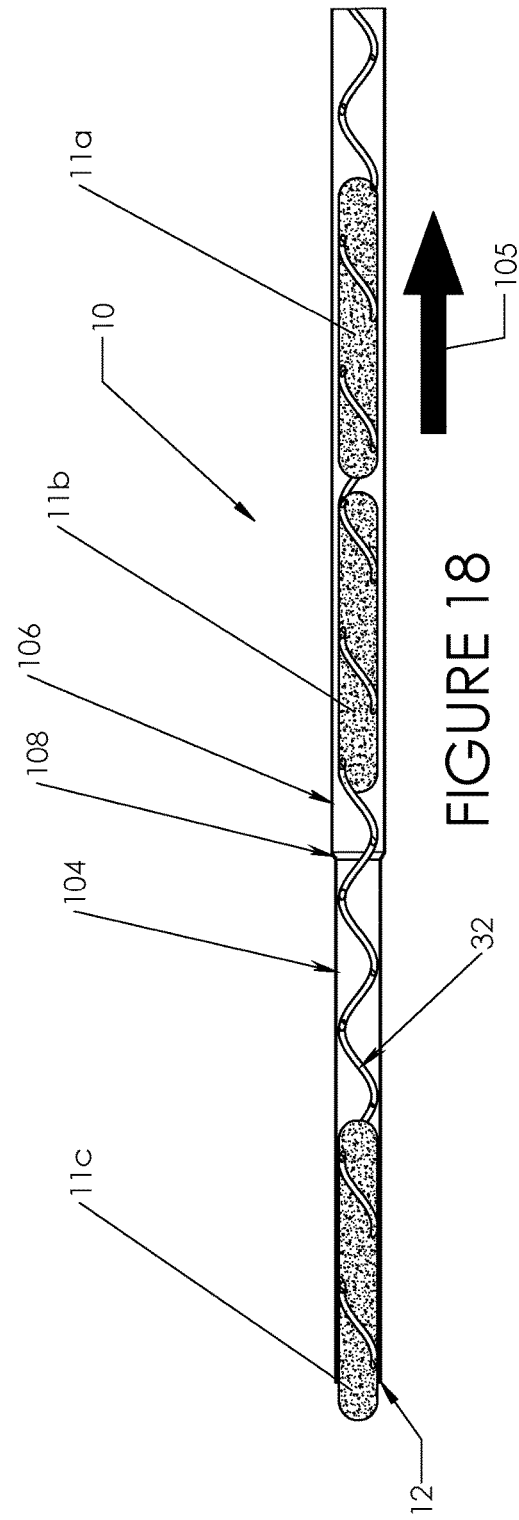

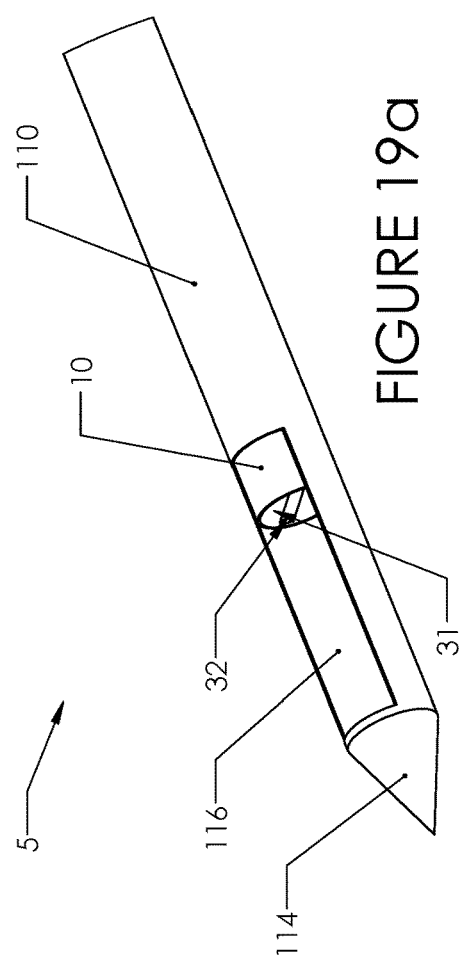
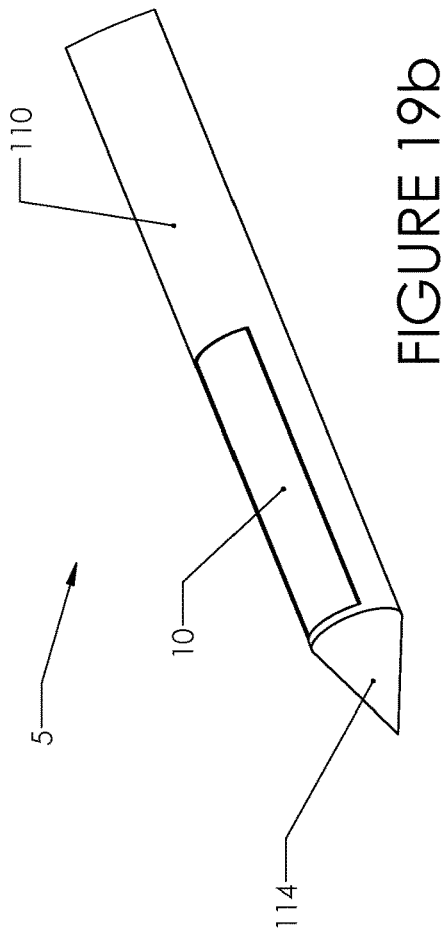

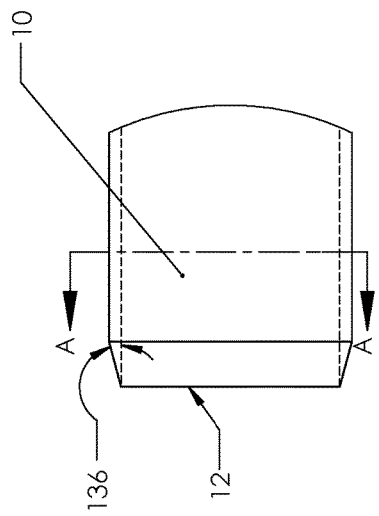
FIGURE 21a
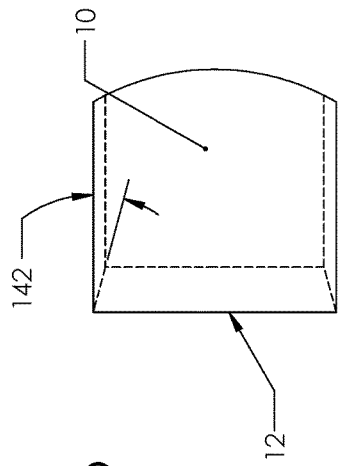
FIGURE 21c
FIGURE 21b
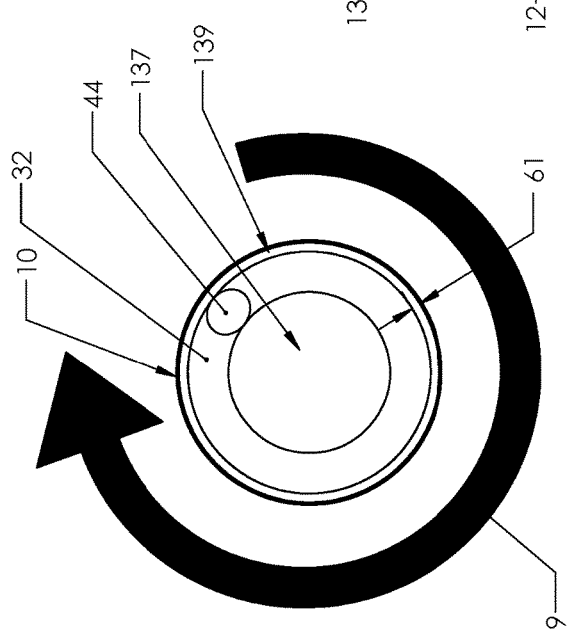
FIGURE 20

SECTION A-A

SECTION A-A

SECTION A-A

SECTION A-A

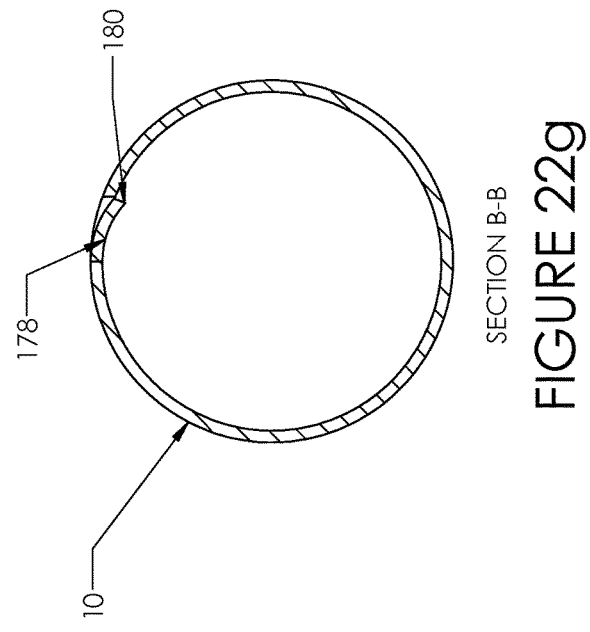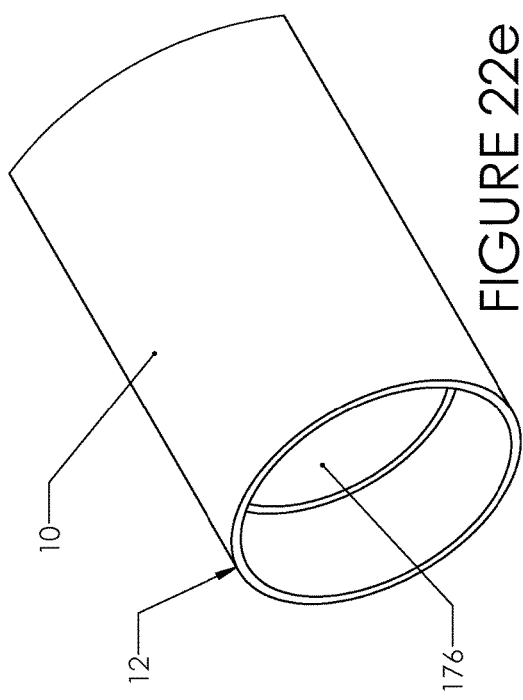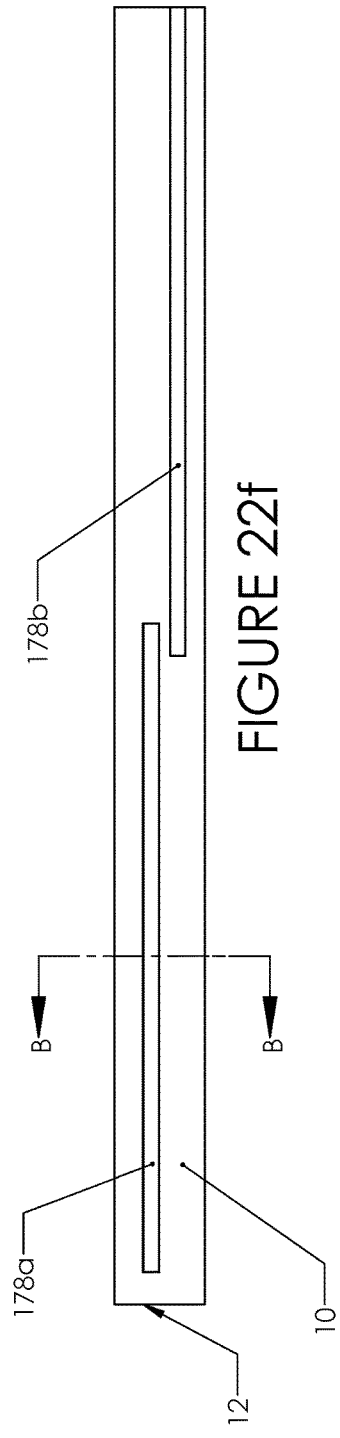

TISSUE REMOVAL DEVICE AND METHOD OF USE

CROSS-REFERENCE TO RELATED APPLICATIONS

This application is a continuation of U.S. application Ser. No. 13/653,395 filed Oct. 16, 2012, which is a continuation of U.S. Pat. No. 8,317,727 issued on Nov. 27, 2012 (U.S. application Ser. No. 13/452,863 filed on Nov. 16, 2011), which is a continuation-in-part of PCT International Application No. PCT/US 2011/061089 filed Nov. 16, 2011, which claims the benefit of U.S. Provisional Application No. 61/415,850 filed Nov. 21, 2010, which are all incorporated by reference herein in their entireties.

BACKGROUND OF THE INVENTION

Field of the Invention

This invention relates to medical instrumentation. More particularly, a tool used for acquiring tissue and a method for using the same are disclosed.

Description of the Prior Art

A number of medical procedures require the removal of tissue samples from a patient. These operations can range from the removal of suspicious tissue, as in the biopsy of a cancerous lesion, to cell harvesting, as in a bone marrow donation. A number of different biopsy tools are used for retrieving these tissue samples from patients, falling into two broad categories: Single-Insertion, Single-Sample (SISS) tools and Single-Insertion, Multiple-Sample (SIMS) tools. With an SISS tool, the operator (1) positions the tool; (2) actuates the collection mechanism(s); (3) removes the tool from the patient; (4) removes the sample from the tool; (5) prepares the tool for re-insertion; and (6) inserts the tool into the patient again. This procedure, which may be repeated several times, is time-consuming and traumatic for the patient. SIMS tools can eliminate steps three through six, above.

The mechanisms of SIMS devices are generally more complex and expensive to manufacture than SISS tools. In addition, they are often quite large devices, as a tissue capturing element is often moved fully distally to obtain the sample, then fully proximally to store the tissue sample. Other known devices shorten the device by spiraling the tissue capturing element in the handle. Other known devices use tissue augers to transport the tissue, but these have not yet been employed in a system that can provide large contiguous samples.

Helical, tissue-contacting features can serve many functions in a biopsy tool, from tissue securing to tissue storage. However, an auger system has not yet been employed in a low-cost, easy to use SIMS tool. Moreover, known devices require the internal element to rotate, which typically yields poor sample quality as the internal element must be sufficiently large to transmit the required torque.

SUMMARY OF THE INVENTION

A tool used to obtain multiple tissue samples is disclosed herein. The mechanical transport system of the tool can be comprised of at least two elements engaged with a tissue sample, where at least one of the elements can have a helical feature. Features can be separate elements or shapes or configurations on existing elements. As the outer element rotates, the outer element may core a section of tissue. Additionally, as the elements rotate with respect to each other, the tissue samples can be urged proximally into a collection area where the tissue samples may be deposited, stored, viewed and retrieved.

The outer element can be a spinning transport tube with a sharpened distal edge and may have tissue-engaging features on the internal face of the transport tube. Surface features can include tissue engaging features which may include the internal surface of the transport tube, axially-oriented ribs, spiral or helical ribs, rifling of the tube, an overlapping tube, a ribbon, surface coating, surface texturing, knurling or combinations thereof. These features may be continuous or discontinuous. The internal surface of the transport tube may be smooth with no features. A stationary internal element can be located within the transport tube. The internal element may have a helical geometry. The internal element may have a surface coating or texture which can engage with the tissue sample. The surface coating may be lubricious. As the outer element spins and is advanced into the tissue, the distal edge of the transport tube may core a section of tissue. The tissue sample can engage and spin with the internal surface features of the transport tube prior, concurrently, simultaneously, subsequently or any combination thereof to the tissue sample being removed from the tissue mass from which the tissue sample is being separated. The tissue sample can spin at the same angular velocity as the outer element (i.e., rotationally stationary relative to the outer element) or at a fraction of the angular velocity of the outer element. The sample can be in contact with the internal element. As the sample spins relative to the internal element, the screw-action (i.e., the rotation of the tissue sample against the helical geometry of the rotationally-fixed internal element) may urge the sample proximally into a collection chamber. The collection chamber may be a portion of the outer element or may be a separate element. The contents of the collection chamber may be accessible to the operator at any time. The collected samples may be stored in the sequence of the acquisition of the samples. The tube, or outer element, can be transparent or translucent. The tube can have a section that can be transparent, translucent or open. The sample may be viewed through the tube.

The samples can be stored in a collection chamber. The entire chamber or a section of the chamber may be transparent, translucent, or open. The samples can be removed by cutting the tube or chamber. The chamber may be always open to the atmosphere or have a protective covering which may be moved to provide access to the samples. The collection chamber or a removable bladder in the reservoir of the collection chamber may dissolve when exposed to a liquid, such as formalin. For example, the collection chamber or the bladder can be made from wax, urate or urate crystals.

The internal element may be removed from the device. The internal element may be removed to provide a larger pathway within the tube. The internal element may be removed to access any samples that may be retained on the internal element. The internal element may be replaced with a different helical element or tool.

The device may be used with a coaxial introducer. Prior to sampling, the coaxial introducer and trocar may be positioned adjacent to the lesion and then the biopsy tool may be introduced through the coaxial introducer. The biopsy tool may be secured to the coaxial introducer, such as with a luer connection.

The tissue samples may be rotationally stationary, or nearly rotationally stationary, relative to the internal element. A spinning outer element may be composed of at least a transport tube. The transport tube can have a sharp distal edge and a spiral feature on the internal face. Nested within the transport tube, the internal element can be a stationary wire with a rectangular cross-section which can pierce the tissue. As the transport tube spins and is advanced into the tissue, the transport tube may core a section of tissue. The internal element can prevent rotation of the sample relative to the internal element without restricting axial motion of the tissue sample. As the spiral feature on the outer element spins relative to the tissue sample, the spiral feature can force the sample proximally into a collection chamber.

The tissue transport systems described above may be used in a side-cutting tool. For instance, a stationary tube may have a closed distal end functioning as a trocar. Proximal to the closed end may be a window cut into the wall of the tube that could allow passage of tissue samples into the inner lumen. A second transport tube may be placed concentrically inside the stationary tube, such that the radial gap between them is less than about 0.1 mm (0.005 in), but large enough such that the second transport tube and the stationary tube can move freely relative to each other. The internal transport tube may be actuated forward or backward to control movement of tissue through the window. A vacuum may be applied to draw tissue through the window. The actuation of the internal transport tube to close the window may sever any tissue from the mass of tissue that has passed through the window. A tissue transport system, as described herein, could then transport the samples proximally, where the internal transport tube may be spun relative to a third internal element.

BRIEF DESCRIPTION OF THE DRAWINGS

FIG. 1 is an illustrative isometric view of a variation of the tool.

FIG. 2 is an illustrative isometric view of the tool in FIG. 1 with an illustrative cutout in a transport tube, showing a helical element located inside and a sample being transported proximally.

FIG. 3 illustrates a drive mechanism for the tool illustrated in FIG. 1 and FIG. 2.

FIG. 4a and FIG. 4b illustrate variations of the helical element used in the tool.

FIG. 5a, FIG. 5b and FIG. 5c illustrate a side view of the distal end of the device being used to core and transport a tissue sample. The spinning transport tube has been shown in cross-section.

FIG. 8 illustrates a side-view of the distal end of the device transporting a sample proximally. The spinning transport tube is shown in cross-section.

FIG. 9 is an isometric view of the distal end of the transport tube, illustrating internal surface features of the element.

FIG. 10 is a transparent side view of the distal end of the transport tube, illustrating internal surface features of the element.

FIG. 14a, FIG. 14b and FIG. 14c illustrate a method for removing the inner element from the device.

FIG. 15 is a side view of the distal end of a variation of the inner element.

FIG. 16a is a side view of the distal end of a variation of the inner element.

FIG. 16b is a proximal facing view of the design illustrated in FIG. 16a.

FIG. 16c is a proximal facing view of a variation of the inner element.

FIG. 16d is a proximal facing view of the design illustrated in FIG. 16b assembled with the transport tube and transporting a tissue sample.

FIG. 16e is a proximal facing view of the design illustrated in FIG. 16c assembled with the transport tube and transporting a tissue sample.

FIG. 17 is a side view of the distal end of a trocar which may be used in conjunction with the device.

FIG. 18 is a side view of the distal end of the device, where the storage chamber is integrated within the transport tube. The transport tube is shown in cross-section.

FIG. 19a and FIG. 19b illustrate an isometric view of the distal end of a side-cutting variation of the tool. FIG. 19a illustrates the tool configured to accept tissue. FIG. 19b illustrates the tool configured for insertion or tissue-transporting.

FIG. 20 is a proximal facing view of the transport tube and helical element.

FIG. 21a, FIG. 21b and FIG. 21c are transparent side views illustrating variations of the distal end of the transport tube.

FIGS. 22a through 22d are variations of cross-section A-A of FIG. 21a.

FIG. 22e is an isometric view of a variation of the distal end of the transport tube.

FIG. 22f is a side view of a variation of the distal end of the transport tube.

FIG. 22g is a variation of cross-section B-B of FIG. 22f.

FIG. 23a is a side view of a tissue sample and FIG. 23b is a cross-section C-C of FIG. 23a.

DETAILED DESCRIPTION

Figure 6:
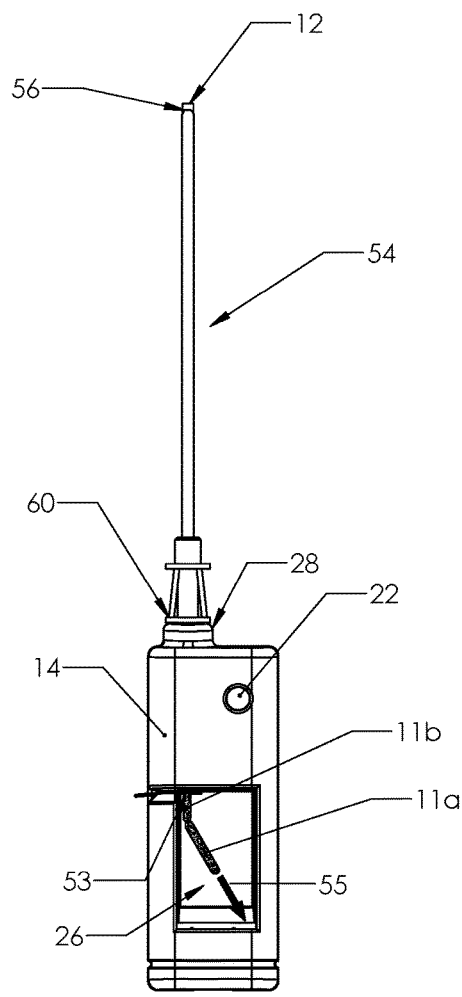
FIG. 6 illustrates a second sample being deposited in the collection chamber of the device. The device also has a coaxial introducer secured to the distal end of the handle.

FIG. 1 illustrates a tool 5. The tool 5 may be sterilized. The tool 5 may have a handle 6 and a tissue transport system 7. The handle 6 can have a handle top portion 14 and a handle bottom portion 16, or a handle left portion and a handle right portion. The handle top portion 14 and handle bottom portion 16 may be joined together to form an ergonomic handle which the operator may hold. The handle top portion 14 and handle bottom portion 16 may be injection molded. The tissue transport system 7 can have a tissue-engaging first external outer element and a tissue-engaging second internal inner element. The tissue-engaging first element (e.g., a tissue-engaging outer element) can be radially outside of the tissue-engaging second element (e.g., a tissue-engaging inner element). The tissue-engaging first element can be or have a transport tube 10. The tissue-engaging inner element can be or have a coiled helical element 32, spiral element 74, flat stationary element 78, curved stationary element 86, or combinations thereof. The coiled helical element 32 can be greater than about 50%, more narrowly greater than about 75%, yet more narrowly greater than or equal to about 100% of the length of a lumen of the transport tube 10. The transport tube 10 can be rotatable or rotationally-fixed with respect to the handle 6. The transport tube 10 can extend distally from the handle 6 and can have a terminal distal end 12. The transport tube 10 may rotate or spin about an axis 8 in a direction 9. The handle 6 can have an electrical connection 18 which can connect with an external power supply. The tool 5 could instead, or in combination with an external power supply, be powered with internal batteries, mechanically, hydraulically or pneumatically. A cover 20 may enclose the samples in a collection chamber 26, shown in FIG. 2. The cover 20 may be removed or adjusted to provide physical access to the samples stored in the collection chamber 26. The cover 20 can be transparent. The rotation of the transport tube 10 may be controlled by actuating a button 22. A first groove 24 can be used to secure a flexible sheath, for example, that can be used to isolate the sterile field from a power cord. The flexible sheath may be, for example, a 0.05 mm (0.002 in) thick open topped, cut-to-length polyethylene bag.

FIG. 2 illustrates that the tool 5 can have a tissue-engaging second element, such as the helical element 32. The helical element 32 can be rotatable or rotationally-fixed with respect to the handle 6. The helical element 32 and the transport tube 10 can transport a sample 11 (e.g., a tissue) proximally in a direction 35. The cover 20 can be opened or removed, for example, to access the collection chamber 26. In FIG. 2, the cover 20 is not shown. The helical element 32 may extend to within about ±3 mm (±0.12 in) of the distal end 12 of the transport tube 10. The handle may also feature a handle connector 28. The handle connector 28 may be formed by the handle top portion 14, handle bottom portion 16, or any combination thereof. The handle connector 28, which may be a luer fitting, may be used to secure other components to the tool, such as a coaxial introducer. The proximal end of the helical element 32 may feature an arm 33. The handle 6 can have a second groove 30 that can be formed between or across the handle top and bottom portions 14, 16 or within one portion 14 or 16, individually. The arm 33 may be secured to the handle 6 by wedging or friction fitting the arm 33 into the second groove 30. The arm 33 can be longitudinally interference fit into the second groove 30. The arm 33 may be secured to the handle by the cover 20. The arm 33 may be secured to the cover 20. The sample 11 can be forced and transported proximally in the direction 35 along the inside of the transport tube 10, from the distal end 12 towards the collection chamber 26. The sample 11 may be obtained, transported, deposited into the collection chamber 26, or combinations thereof, with or without applying suction to the proximal end of the transport tube 10 or collection chamber 26. The sample 11 may be obtained, transported, deposited into the collection chamber 26, or combinations thereof, without or with a pressure differential between the terminal distal end 12 and a proximal open port 53. For example biological pressure from lungs or vessels at the terminal end of the transport tube 10 can exert a higher pressure than the external environment in fluid communication with the proximal end of the transport tube, for example pushing the tissue sample proximally in the transport tube.

FIG. 3 shows a drive system which may be used to spin the transport tube 10. A motor 34 can spin when the button 22 is actuated. The motor 34 may be powered by electricity. The motor 34 can be a DC brushed motor. The motor 34 may be driven pneumatically, hydraulically, mechanically or any combination thereof. A first pulley 36 may be secured to a motor shaft 37. The first pulley 36 may be a timing belt pulley with a pitch of about 2 mm (0.08 in). The first pulley 36 may transmit torque to a second pulley 38 via a timing belt 40. The first and second pulleys 36 and 38 may be different sizes. The pulley 38 may be secured to the transport tube 10.

FIG. 4a shows that the helical element 32 may have a pitch 42 that is constant along the length of the helical element 32. The pitch 42 of the helical element 32 may be from about 7 mm (0.28 in.) to 20 mm (0.8 in.). The pitch 42 of the helical element may be specified for certain application, such as different tissue types. For example, the helical element 32 can be removed from the tool 5 and replaced with a second helical element 32 of a different configuration from the original helical element 32 (e.g., to be used in harder or softer tissue than the original helical element 32 is intended to be used on). Configurations of the helical element 32 may have a different pitch, wireform, surface feature, coating, cross-sectional shape, modulus of elasticity, or combinations thereof. The wire used to form the helical element 32 may have a round cross-section. The helical element 32 can be made from wire with a cross-section that is circular, angular, rectangular, triangular or combinations thereof (e.g., changing along the length of the wire). The helical element 32 may have a sharpened distal end 44. The helical element 32 may have the arm 33. The arm 33 may be used to secure the helical element 32 to the handle 6. The arm 33 may hold the inner element, such as the helical element 32, longitudinally stationary relative to the outer element, such as the transport tube 10. The arm 33 may be used to manipulate (e.g., rotate and/or translate) the helical element 32, during manufacturing, assembly and use.

FIG. 4b shows that the helical element 32 may have a varied pitch. For example, the helical element 32 may transition from a longer distal first pitch 43 to a shorter proximal second pitch 45. The distal pitch 43 can be shorter than proximal pitch 45. An intermediate length between the distal pitch 43 and the proximal pitch 45 can have a different pitch than the proximal and distal sections (e.g., the distal pitch 43 can be equal to the proximal pitch 45 which can both be longer or shorter than the pitch of the intermediate length). The transition between first pitch 43 and second pitch 45 may be smooth (e.g., continuously tangential) or abrupt (e.g., discrete).

The pitch of the helical element (such as pitches 42, 43, 45 or combinations thereof) may be larger than about 5 mm (0.20 in), yet more narrowly larger than about 6 mm (0.24 in), yet more narrowly larger than about 7 mm (0.28 in), yet more narrowly larger than about 8 mm (0.31 in), yet more narrowly larger than about 9 mm (0.35 in), yet more narrowly larger than about 10 mm (0.39 in), yet more narrowly larger than about 11 mm (0.43 in), yet more narrowly larger than about 12 mm (0.47 in), yet more narrowly larger than about 20 mm (0.8 in). The pitch of the helical element (such as pitches 42, 43, 45 or combinations thereof) may be less than about 20 mm (0.8 in), yet more narrowly less than about 12 mm (0.47 in), yet more narrowly less than about 11 mm (0.43 in), yet more narrowly less than about 10 mm (0.39 in), yet more narrowly less than about 9 mm (0.35 in), yet more narrowly less than about 8 mm (0.31 in), yet more narrowly less than about 7 mm (0.28 in), yet more narrowly less than about 6 mm (0.24 in), yet more narrowly less than about 5 mm (0.20 in).

The helical element 32 or any or all elements of the tool and/or other tools or apparatuses described herein can be made from or coated with, for example, single or multiple stainless steel alloys, steel, spring steel, nickel titanium alloys (e.g., Nitinol), cobalt-chrome alloys (e.g., ELGILOY® from Elgin Specialty Metals, Elgin, Ill.; CON-ICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy), tungsten-rhenium alloys, polymers such as polyethylene teraphathalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), Parylene poly(p-xylylene) polymers, Parylene N, Parylene C, Parylene D, expanded PTFE (ePTFE), polyether ketone (PEK), polyether ether ketone (PEEK), polycarbonate (PC), Acrylonitrile Butadiene Styrene (ABS), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), Nylon, Vinyl, polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone), a material with high strength (60 ksi) and biocompatibility, any of the other materials listed herein or combinations thereof. Examples of radiopaque materials are barium sulfate, zinc oxide, titanium, stainless steel, nickel-titanium alloys, tantalum and gold. The device can be made from substantially 100% PEEK, substantially 100% titanium or titanium alloy, or combinations thereof.

FIG. 5a, FIG. 5b and FIG. 5c illustrate a variation of a method for using the tissue transport system 7. FIG. 5a, FIG. 5b and FIG. 5c show how the tool 5 may be manipulated to cut off a tissue sample from a mass of tissue 48. The tissue mass may be located in a living or dead plant or animal, such as a tumor in a human breast. FIG. 5a illustrates that the transport tube 10 can be advanced (e.g., translated) relative to and into the tissue 48 in a direction 47. The transport tube 10 can have an open distal end 12. The transport tube 10 can receive a portion of the tissue 48 into a distal open port 31 at the distal end 12. The transport tube 10 can be rotated or spun relative to the tissue 48 concurrent with being translated into the tissue 48. The transport tube 10 can core the tissue 48. A tissue sample 11 can be a partially cored, severed or cut sample. The sample 11 may be in contact with the internal face and/or surface features of the transport tube 10. The sample 11 may still be connected to the mass of tissue 48. The sample 11 can simultaneously engage with the helical element 32 while being attached to the mass of tissue 48 and in contact with the internal face and/or surface features of the transport tube 10. The sample 11 can screw into the helical element 32 as the transport tube 10 is rotated and advanced into the mass of tissue 48.

FIG. 5b shows that the transport tube 10 may be rotated in a direction 49 to pinch the partially cored tissue sample 11 at a pinch point 52. While still attached to the mass of tissue 48, the portion of tissue in the transport tube 10 can remain substantially rotationally fixed with respect to the helical element 32. The terminal end of the distal end 12 of the transport tube 10 can sever a tissue sample 11 from the mass of tissue 48. Alternatively or in addition to pinching, the sample 11 may be severed from the mass of tissue 48 by continuing to spin the transport tube 10 while not advancing the transport tube 10 distally, by continuing to spin the transport tube 10 while retreating the transport tube 10 proximally, by applying a lateral force on the tool 5 while the transport tube 10 continues to spin or combinations thereof. Separation of the tissue sample 11 from the mass of tissue 48 and transportation of the sample 11 along the transport tube 10 can be atraumatic to the sample 11. For example, the sample 11 can be un-macerated, unsplit, maintain a contiguous cross-section, or combinations thereof.

FIG. 5c shows that after the tissue sample 11 is detached or severed from the mass of tissue 48, continuing to spin the transport tube 10 may then transport the tissue sample 11 proximally along the internal length of the transport tube 10, as shown. The tissue sample 11 may rotate or spin partially or completely with transport tube 10. The tissue sample 11 may rotate or spin relative to the helical element 32. The relative rotational motion between the tissue sample 11 and the helical element 32 may result in a forced translation of sample 11 in proximal direction 51 along the longitudinal axis 8 of the transport tube 10.

FIG. 6 shows how the tissue samples collected in FIG. 5a, FIG. 5b and FIG. 5c may be stored in the collection chamber 26. The tissue transport system 7 can continue to advance the tissue sample 11 along the length of the transport tube 10 proximally as the tissue sample 11 enters the collection chamber 26. As the tissue sample 11 emerges from the proximal open port 53 at the proximal end of the transport tube 10, the tissue sample 11 can enter and is delivered and deposited into the collection chamber 26.

For example, a proximal tissue sample 11a can exit the transport tube 10 into the collection chamber 26. A distal tissue sample 11b can be cored and severed from the mass of tissue 48 after the proximal tissue sample 11a is cored and severed from the mass of tissue 48. The distal tissue sample 11b can be proximally advanced along the length of the transport tube 10. The distal tissue sample 11b can abut and push the proximal tissue sample 11a in a proximal direction 55. The proximal tissue sample 11b can be pushed completely out of the transport tube 10 and into the collection chamber 26. The tissue samples 11 may be stored in the collection chamber 26 in chronological sequence of collection. After the tissue sample 11 emerges completely from the transport tube 10, the tissue sample 11 can cease to move unless contacted by an external force, such as the motion of another tissue sample 11.

FIG. 6 illustrates that the tool 5 can include or be removably attached to a coaxial introducer 54, such as Bard C1213B, manufactured by Bard Biopsy Systems of Arizona. An introducer connector 60 on the coaxial introducer 54 may be detachably secured to the handle 6 at handle connector 28. The distal end 12 of the transport tube 10 may extend past an introducer distal edge 56 of the coaxial introducer 54. The coaxial introducer 54 may protect the mass of tissue 48 other than the sample 11 from most or all of the transport tube 10. The coaxial introducer 54 may provide a bearing surface for the transport tube 10.

Figure 7:
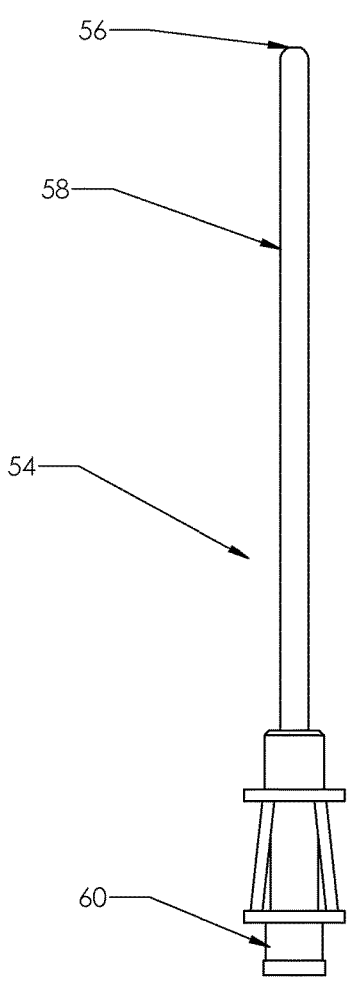
FIG. 7 illustrates a coaxial introducer which may be used in conjunction with the device.

FIG. 7 shows that the coaxial introducer 54 can have an introducer tube 58. The introducer tube 58 can fit over the transport tube 10. The radial clearance between the introducer tube 58 and the transport tube 10 may be larger than about 0.02 mm (0.001 in), more narrowly larger than about 0.1 mm (0.004 in), yet more narrowly larger than about 0.2 mm (0.008 in), yet more narrowly larger than about 0.3 mm (0.012 in), or yet more narrowly larger than about 0.4 mm (0.015 in). The radial clearance between the introducer tube 58 and the transport tube 10 can be smaller than about 0.4 mm (0.015 in), more narrowly smaller than about 0.3 mm (0.012 in), yet more narrowly smaller than about 0.2 mm (0.008 in), yet more narrowly smaller than about 0.1 mm (0.004 in), or yet more narrowly smaller than about 0.02 mm (0.001 in). The introducer tube 58 may have the sharp introducer distal edge 56.

The coaxial introducer 54 may have the introducer connector 60. The introducer connector 60 may be a luer fitting and may mate with the handle connector 28. The mating connectors 28 and 60 may be threaded in a direction that tightens the mating connection as the transport tube 10 spins. The coaxial introducer 54 may be positioned in the tissue 48 with a sharp trocar 94 or stylet located within the introducer tube 58. After the introducer distal edge 56 is placed adjacent to the target, the trocar 94 may be removed and replaced with the tool 5. The coaxial introducer 54 may be echogenic and have position markings to guide the operator.

FIG. 8 illustrates that the helical element 32 may have a clearance fit 61 with the transport tube 10. For example, the clearance fit 61 can be large enough that the components can spin freely relative to each other. The clearance fit 61 can be larger than about 0.02 mm (0.001 in), more narrowly larger than about 0.1 mm (0.004 in), yet more narrowly larger than about 0.2 mm (0.008 in), yet more narrowly larger than about 0.3 mm (0.012 in), or yet more narrowly larger than about 0.4 mm (0.015 in). The clearance fit 61 can be smaller than about 0.4 mm (0.015 in), more narrowly smaller than about 0.3 mm (0.012 in), yet more narrowly smaller than about 0.2 mm (0.008 in), yet more narrowly smaller than about 0.1 mm (0.004 in), or yet more narrowly smaller than about 0.02 mm (0.001 in). The helical element 32 can urge a tissue sample 11 in a proximal direction 63 as the tissue sample 11 spins relative to the helical element 32. The tissue sample 11 can be cored, severed, and transported from the mass of tissue 48 to the collection chamber 26 quickly, such as in less than about 6 seconds, more narrowly in less than about 3 seconds, for example to minimize trauma to both patient, the mass of tissue 48, and the tissue sample 11.

The distal end 44 of the helical element 32 may extend past the distal end 12 of the transport tube 10, as illustrated in FIG. 8. The distal end 44 may terminate flush (i.e., terminating at the same length) with the distal end 12. The distal end 44 may terminate proximal to the distal end 12. The distance between the distal ends 12 and 44 may be larger than about 0.5 mm (0.02 in), yet more narrowly larger than about 1 mm (0.04 in), yet more narrowly larger than about 1.5 mm (0.06 in), yet more narrowly larger than about 2 mm (0.08 in), yet more narrowly than about 2.5 mm (0.10 in), yet more narrowly larger than about 3 mm (0.12 in), yet more narrowly larger than about 3.5 mm (0.14 in), yet more narrowly larger than about 4 mm (0.18 in), yet more narrowly larger than about 4.5 mm (0.18 in), yet more narrowly larger than about 5 mm (0.20 in), yet more narrowly larger than about 6 mm (0.24 in), yet more narrowly larger than about 7 mm (0.28 in), yet more narrowly larger than about 10 mm (0.39 in). The distance between the distal ends 12 and 44 may be less than about 10 mm (0.39 in), yet more narrowly less than about 7 mm (0.28 in), yet more narrowly less than about 6 mm (0.24 in), yet more narrowly less than about 5 mm (0.20 in), yet more narrowly less than about 4.5 mm (0.18 in), yet more narrowly less than about 4 mm (0.18 in), yet more narrowly less than about 3.5 mm (0.14 in), yet more narrowly less than about 3 mm (0.12 in), yet more narrowly less than about 2.5 mm (0.10 in), yet more narrowly less than about 2 mm (0.08 in), yet more narrowly less than about 1.5 mm (0.06 in), yet more narrowly less than about 1 mm (0.04 in), yet more narrowly less than about 0.5 mm (0.02 in).

During transport from the distal end 12 of the transport tube 10 to the collection chamber 26, the tissue sample 11 can have a linear velocity of greater than about 1 cm/sec (0.4 in/sec), yet more narrowly larger than about 2.5 cm/sec (1.0 in/sec), yet more narrowly larger than about 5 cm/sec (1.9 in/sec), yet more narrowly larger than about 7.5 cm/sec (2.9 in/sec), or yet more narrowly larger than about 10 cm/sec (3.9 in/sec). During transport from the distal end 12 of the transport tube 10 to the collection chamber 26, the tissue sample 11 can have a linear velocity of less than about 10 cm/sec (3.9 in/sec), yet more narrowly less than about 7.5 cm/sec (2.9 in/sec), yet more narrowly less than about 5 cm/sec (1.9 in/sec), yet more narrowly less than about 2.5 cm/sec (1.0 in/sec), or yet more narrowly less than about 1 cm/sec (0.4 in/sec). The linear velocity of the sample may change along the length of the transport tube 10, for example if the helical element 32 has a varying pitch.

The transport tube 10 may spin or rotate at a velocity relative to the handle 6 of greater than about 1,000 rpm, yet more narrowly larger than about 2,500 rpm, yet more narrowly larger than about 3,000 rpm, yet more narrowly larger than about 4,000 rpm, yet more narrowly larger than about 5,000 rpm, yet more narrowly larger than about 7,500 rpm, yet more narrowly larger than about 10,000 rpm. The transport tube 10 may spin or rotate at a velocity relative to the handle 6 of less than about 10,000 rpm, yet more narrowly less than about 7,500 rpm, yet more narrowly less than about 5,000 rpm, yet more narrowly less than about 4,000 rpm, yet more narrowly less than about 3,000 rpm, yet more narrowly less than about 2,500 rpm, yet more narrowly less than about 1,000 rpm.

The tissue-engaging first element may spin or rotate relative to the tissue-engaging second element at a relative velocity of greater than about 1,000 rpm, more narrowly larger than about 2,500 rpm, yet more narrowly larger than about 3,000 rpm, yet more narrowly larger than about 4,000 rpm, yet more narrowly larger than about 5,000 rpm, yet more narrowly larger than about 7,500 rpm, or yet more narrowly larger than about 10,000 rpm. The tissue-engaging first element may spin or rotate relative to the tissue-engaging second element at a relative velocity of less than about 10,000 rpm, more narrowly less than about 7,500 rpm, yet more narrowly less than about 5,000 rpm, yet more narrowly less than about 4,000 rpm, yet more narrowly less than about 3,000 rpm, yet more narrowly less than about 2,500 rpm, or yet more narrowly less than about 1,000 rpm. The relative rotational speed between the tissue-engaging first element and the tissue-engaging second element may vary, for example the relative rotational speed may be higher during tissue coring than tissue transport.

The ratio of rotation of the tissue sample 11 to the transport tube 10 may be greater than about 10% (e.g., the sample 11 may spin or rotate at a rate greater than about 10% of the rpm of the transport tube 10), more narrowly greater than about 25%, yet more narrowly greater than about 50%, yet more narrowly greater than about 75%, yet more narrowly greater than about 99% (e.g.—the sample 11 and the transport tube 10 are spinning together at approximately the same rate, with very little rotational slippage). The ratio of rotation of sample 11 to the transport tube 10 may be less than about 100% (e.g.—the sample 11 and the transport tube 10 are spinning together at approximately the same rate, with very little rotational slippage), more narrowly less than about 75%, yet more narrowly less than about 50%, yet more narrowly less than about 25%, yet more narrowly less than about 10% (e.g., the sample 11 may spin or rotate at a rate less than about 10% of the rpm of the transport tube 10).

The coefficient of friction between the sample 11, the helical element 32, the transport tube 10, tissue-engaging surface features or any combination thereof may be greater than about 0.05, more narrowly greater than about 0.1, yet more narrowly greater than about 0.2, yet more narrowly greater than about 0.4, yet more narrowly greater than about 0.6, yet more narrowly greater than about 0.8, yet more narrowly greater than about 1.0. The coefficient of friction between the sample 11, the helical element 32, the transport tube 10, tissue-engaging surface features or any combination thereof may be less than about 1.0, more narrowly less than about 0.8, yet more narrowly less than about 0.6, yet more narrowly less than about 0.4, yet more narrowly less than about 0.2, yet more narrowly less than about 0.1, or yet more narrowly less than about 0.05.

The internal diameter of the transport tube 10 may be larger than about 0.5 mm (0.02 in), more narrowly larger than about 1 mm (0.04 in), yet more narrowly larger than about 1.5 mm (0.06 in), yet more narrowly larger than about 2 mm (0.08 in), yet more narrowly than about 2.5 mm (0.10 in), yet more narrowly larger than about 3 mm (0.12 in), yet more narrowly larger than about 3.5 mm (0.14 in), yet more narrowly larger than about 4 mm (0.18 in), yet more narrowly larger than about 4.5 mm (0.18 in), yet more narrowly larger than about 5 mm (0.20 in), yet more narrowly larger than about 6 mm (0.24 in), yet more narrowly larger than about 7 mm (0.28 in), or yet more narrowly larger than about 10 mm (0.39 in). The internal diameter of the transport tube 10 may be less than about 10 mm (0.39 in), more narrowly less than about 7 mm (0.28 in), yet more narrowly less than about 6 mm (0.24 in), yet more narrowly less than about 5 mm (0.20 in), yet more narrowly less than about 4.5 mm (0.18 in), yet more narrowly less than about 4 mm (0.18 in), yet more narrowly less than about 3.5 mm (0.14 in), yet more narrowly less than about 3 mm (0.12 in), yet more narrowly less than about 2.5 mm (0.10 in), yet more narrowly less than about 2 mm (0.08 in), yet more narrowly less than about 1.5 mm (0.06 in), yet more narrowly less than about 1 mm (0.04 in), or yet more narrowly less than about 0.5 mm (0.02 in).

The wall thickness of the transport tube 10 may be larger than about 0.05 mm (0.002 in), more narrowly larger than about 0.10 mm (0.004 in), yet more narrowly larger than about 0.15 mm (0.006 in), yet more narrowly larger than about 0.20 mm (0.008 in), yet more narrowly larger than about 0.30 mm (0.012 in), yet more narrowly larger than about 0.50 mm (0.020 in), yet more narrowly larger than about 0.70 mm (0.028 in), or yet more narrowly larger than about 1.00 mm (0.039 in). The wall thickness of the transport tube 10 may be less than about 1.00 mm (0.039 in), yet more narrowly less than about 0.70 mm (0.028 in), yet more narrowly less than about 0.50 mm (0.020 in), yet more narrowly less than about 0.43 mm (0.017 in), yet more narrowly less than about 0.30 mm (0.012 in), yet more narrowly less than about 0.20 mm (0.008 in), yet more narrowly less than about 0.15 mm (0.006 in), yet more narrowly less than about 0.10 mm (0.004 in), or yet more narrowly less than about 0.05 mm (0.002 in).

The wire thickness of the helical element 32 may be larger than about 0.05 mm (0.002 in), more narrowly larger than about 0.10 mm (0.004 in), yet more narrowly larger than about 0.15 mm (0.006 in), yet more narrowly larger than about 0.20 mm (0.008 in), yet more narrowly larger than about 0.30 mm (0.012 in), yet more narrowly larger than about 0.50 mm (0.020 in), yet more narrowly larger than about 0.70 mm (0.028 in), or yet more narrowly larger than about 1.00 mm (0.039 in). The wire thickness of the helical element 32 may be less than about 1.00 mm (0.039 in), more narrowly less than about 0.70 mm (0.028 in), yet more narrowly less than about 0.50 mm (0.020 in), yet more narrowly less than about 0.30 mm (0.012 in), yet more narrowly less than about 0.20 mm (0.008 in), yet more narrowly less than about 0.15 mm (0.006 in), yet more narrowly less than about 0.10 mm (0.004 in), or yet more narrowly less than about 0.05 mm (0.002 in). The wire thickness can be about 0.4 mm (0.016 in.), 0.43 mm (0.017 in.), or combinations thereof.

The tissue sample 11 can rotate none at all or almost none relative to the non-helical element, such as the transport tube 10 in some configurations. The internal face of the transport tube 10 or any or all elements of the tool and/or other tools or apparatuses described herein can have surface features. Surface features may include tissue engaging features which can be one or more spiral and/or axial ribs, knurling, ridges, spines, barbs, coatings, textured surface, overlapping tube and/or tubes, ribbon and/or ribbons, or combinations thereof. Surface features can be configured to engage or not engage the tissue. The surface features can be continuous or discontinuous along the surface (e.g., along a portion of the length, a portion of the arc of the wall, or combination thereof) of the tissue-engaging first and/or second elements.

FIG. 9 illustrates that the inner surface of the transport tube 10 can comprise one or more axially oriented rib 62. The rib 62 can increase torsional traction (e.g., deliver rotational force) between the tissue sample 11 and the transport tube 10. The rib 62 may not significantly impact traction (e.g., delivering no longitudinal force and providing minimal or no counter force in the longitudinal direction) in the longitudinal direction between the tissue sample 11 and the rib 62. The transport tube 10 may have one rib 62, more narrowly more than about five ribs 62, yet more narrowly more than about ten ribs 62, yet more narrowly more than about fifteen ribs 62. The transport tube 10 may have about twenty ribs 62, more narrowly less than about fifteen ribs 62, yet more narrowly less than about ten ribs 62, yet more narrowly less than about five ribs 62. The rib 62 can be integrated with the transport tube 10, such as by being formed by being machined, wire EDM, extruded or stamped from the same block of material, and/or separate elements which can be secured to the transport tube 10 with glue, welding, brazing, epoxy, one or more rivets, friction (e.g., crimping; or a spring radially tightened to under a relaxed diameter of the spring which is then released into the transport tube 10 having a diameter less than the relaxed diameter), or combinations thereof. The transport tube 10 can be absent, for example, if the elements of the rib 62 are rigid, as in a rigid coil. The rib 62 can be formed by removing material from the transport tube 10. For instance, the rib 62 can be slots machined or rifled in the transport tube 10. The rib 62 may be formed by compressing the transport tube 10, raising or stretching the surface of the transport tube 10 (e.g., radially inwardly embossing or stamping a compliant material of the transport tube 10), removing material (e.g., wire EDM, EDM, or machining) or any combination thereof.

FIG. 10. illustrates that the internal face of the transport tube 10 can have spiral ribs 64a and 64b. The transport tube 10 can have one spiral rib 64a, or multiple spiral ribs. The direction of the spiral ribs 64 can be opposite that of the internal helical element 32 (e.g., if the internal helical element 32 is oriented clockwise, then the spirals ribs 64a and 64b can be oriented counter-clockwise). Spiral rib distal ends 66a and 66b of the spiral ribs 64a and 64b, respectively, can be sharpened and extend past the tube body distal end 12. The rib distal end 66 can extend distal to the tube body distal end 12. The rib distal end 66 can be flush (i.e., terminating at the same length) with the tube body distal end 12. The rib distal end 66 can terminate proximally to the tube body distal end 12. The distance between the terminal rib distal end 66 and the tube body distal end 12 can be more than 0.2 mm (0.008 in), yet more narrowly more than 0.4 mm (0.016 in), yet more narrowly more than 0.6 mm (0.024 in), yet more narrowly more than 0.8 mm (0.03 in), or yet more narrowly more than 1.0 mm (0.04 in). The distance between the terminal distal end 66 and the distal end 12 can be less than 1.0 mm (0.04 in), more narrowly less than 0.8 mm (0.03 in), yet more narrowly less than 0.6 mm (0.024 in), yet more narrowly less than 0.4 mm (0.016 in), or yet more narrowly less than 0.2 mm (0.008 in). The spiral rib distal ends 66a and 66b can be sharp cutting elements, for example, to core the mass of tissue 48.

Figure 11:
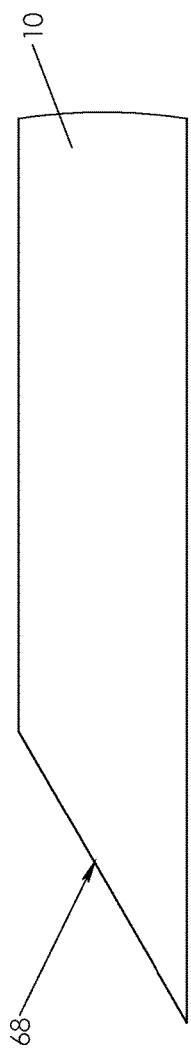
FIG. 11 is a side view of the distal end of the tool illustrating a lancet-like tip.
Figure 12:
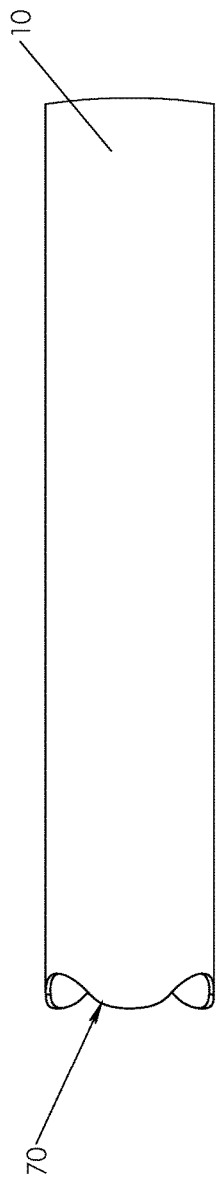
FIG. 12 is a side view of the distal end of the tool illustrating a waved tip geometry.
Figure 13:
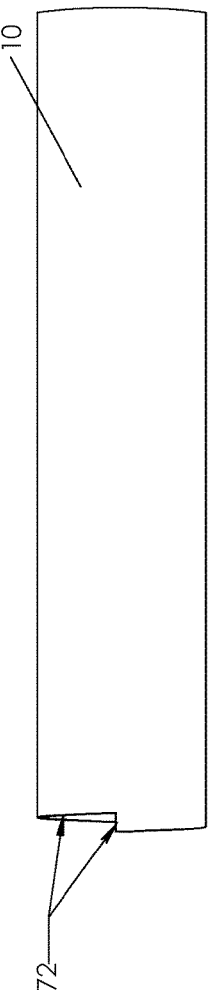
FIG. 13 is a side view of the distal end of the tool illustrating a stepped tip geometry

The distal end 12 of the transport tube 10 may have a bias grind, vet point, lancet point, deflected point, probe point, blunt end, trephine, menghini, razor edge surface, or combinations thereof. The distal end 12 may have a sharpened non-planar profile, as shown in FIG. 11, FIG. 12 and FIG. 13. For instance, FIG. 11 illustrates how the distal end 12 of the transport tube 10 can come to a sharp lancet-like point 68. The tool 5 can be inserted into the mass of tissue 48 of the patient when a trocar is not used, or when a trocar is used. FIG. 12 shows that the distal end 12 may have wave profile 70. FIG. 13 shows that the distal end 12 may have a stepped circumference with sharp edges 72.

FIG. 14a, FIG. 14b and FIG. 14c illustrate how the helical element 32 may be removed from the tool. During sample acquisition, the arm 33 may be secured in the second groove 30. The arm 33 may be rotated in a counter-clockwise direction 71, for example to remove the helical element 32 from the groove 30. Subsequently, the helical element 32 may be pulled proximally out of the transport tube 10 in a direction 73, for example, until the helical element 32 is laterally unconstrained by the transport tube 10 or the remainder of the tool 5, such as by the collection chamber 26. A different helical element 32 (e.g., with a different pitch) or other element, such as spiral element 74, flat stationary element 78, curved stationary element 86, trocar 94, or combinations thereof, can be inserted into the transport tube 10 in a reverse of the method described in FIG. 14a through FIG. 14c. Similarly, any of the tissue-engaging second elements can be removed from the tissue-engaging first element and tool, and be replaced by the same type or a different tissue-engaging second element.

FIG. 15 illustrates a close-up of a spiral element 74. The spiral element 74 can have the same function of the helical element 32 in FIG. 4a. The spiral element 74 may pierce the tissue sample 11. The spiral element 74 may have a smaller outside diameter than helical element 32. The spiral element 74 can be a twisted, flat wire or ribbon as shown in FIG. 15. A terminal distal tip 76 may be sharpened, for example, to allow the spiral element 74 to pierce the tissue 48. The pitch of the spiral element 74 may be similar to the pitches 42, 43, 45 or combinations thereof. A portion of the spiral element 74 may be untwisted, such as on the proximal and/or distal ends of the spiral element 74.

FIG. 16a shows that a flat stationary element 78 can be a straight flat wire or ribbon. The flat stationary element 78 can prevent the tissue sample 11 from spinning relative to the flat stationary element 78. The flat stationary element 78 may be concentric with and/or off-axis from the transport tube 10 (e.g., the flat stationary element 78 may be concentric with the transport tube 10 for a portion of the length). The internal face of the transport tube 10 can comprise a helical feature or element, such as the spiral rib 64 shown in FIG. 10. As the transport tube 10 rotates relative to the flat stationary element 78 and the tissue sample 11, the tissue sample 11 can be urged proximally along axis 8. The flat stationary element 78 can have a sharpened tip 80. The cross-section of the flat stationary element 78 may be rectangular, as shown in FIG. 16b. For example, the thickness of a first side 82 may be about 0.3 mm (0.01 in) and the width of a second side 84 may be about 0.5 mm (0.02 in). The cross-section of the flat stationary element 78 can be circular, angular, rectangular, triangular or combinations thereof (e.g., changing along the length of the flat stationary element 78).

FIG. 16c illustrates that the stationary element may be a curved stationary element 86. The curved stationary element 86 can have an outer surface 90. The outer surface 90 can contact and/or rest on the radially inner surface of the spiral rib 64, or any other surface features which can rotate relative to outer surface 90. The curved stationary element 86 can have bends 88a and 88b extending at an angle (e.g., from about 45 degrees to about 135 degrees) from the outer surface 90. The bends 88a and 88b can engage with the tissue sample 11 to prevent the tissue sample 11 from rotating relative to the curved stationary element 86. The bends 88a and 88b can provide structural rigidity to the curved stationary element 86. The curved stationary element 86 can have one bend 88 or multiple bends 88. The tissue sample 11 may contact the inner surface 92.

FIG. 16d illustrates that the stationary element (shown as flat stationary element 78) can be approximately centered in the transport tube 10. The stationary element may pierce the tissue sample 11. The tissue sample 11 may be in contact with the transport tube 10, internal surface features of the transport tube 10, or a combination thereof. The tissue sample 11 may be in contact with spiral rib 64. The stationary element may be radially spaced ("off-axis") away from axis 8 of the transport tube 10.

FIG. 16e illustrates that the curved stationary element 86 may be positioned off-axis from the transport tube 10. The curved stationary element 86 may be centered or approximately centered with the transport tube 10. The curved stationary element 86 may surround the tissue sample 11, the curved stationary element 86 may fully pierce the tissue sample 11 or a combination thereof (e.g. the position of the curved stationary element 86 relative to the transport tube 10 may vary along the axis 8). The tissue sample 11 may be in contact with the transport tube 10, internal surface features, spiral rib 64 or a combination thereof.

FIG. 17 shows a trocar 94 that can be a sharp stylet. The trocar 94 can be inserted into the coaxial introducer 54, for example before, and/or during, and/or after the coaxial introducer is inserted into the tissue 48. The trocar 94 can be removed from the coaxial introducer before the transport tube 10 is inserted into the coaxial introducer 54.

The trocar 94 may be located in the transport tube 10 while the tool 5 is inserted into the patient and into the tissue 48. The trocar 94 can be removed from the tool 5 during sampling (e.g., coring, severing and translating the tissue sample 11 into the collection chamber 26). The trocar 94 can have a structural rod 96 with a sharpened distal end 100. The trocar 94 may be located adjacent to the tissue-engaging second element, such as concentrically within the helical element 32. The trocar 94 may replace the tissue-engaging second element during insertion of the tool 5 into the tissue 48 and be exchanged with the tissue-engaging second element prior to sampling. The trocar 94 can be advanced along the axis 8, for example, by the rotation of the transport tube 10. The trocar 94 can have bumps 98a and 98b that can extend radially from the outer wall of the trocar 94. The trocar can be without bumps 98. The trocar 94 can be slid concentrically within the transport tube 10 and the helical element 32. The bumps 98a and 98b can engage with the inner surface of the wall of the transport tube 10, with the radial inner surface of the outer element, with surface features of the transport tube 10, with the internal features on the transport tube 10, such as the spiral rib 64, with the helical element 32, with the internal element, with surface features of the helical element 32, or any combination thereof. The trocar 94 may be advanced or retracted along the axis 8, for example, by pressing the button 22 to actuate the motor 34 clockwise or counterclockwise. The helical element 32 may remain in the transport tube 10 when the trocar 94 is inserted in the transport tube 10. For example, the helical element 32 can be positioned between the trocar 94 and the inner wall of the transport tube 10.

FIG. 18 illustrates that the transport tube 10 may store the tissue samples 11a and 11b. The length of the portion of the tool 5 which is inside of the patient can be greater than about 7.5 cm (3 in). The tissue samples 11 may travel at least about 7.5 cm (3 in) to reach the collection chamber 26.

The transport tube 10 may have a transition portion, such as taper 108. The transition portion, such as taper 108, can connect a sample-motility length at the distal end of the tube 10 with a sample-storage length at the proximal end of the tube 10. The sample-motility length can have a smaller diameter distal section 104, high-friction tube section, lower-friction tissue-engaging second element section, surface-featured section, thicker tissue-engaging second element section, or combinations thereof. The sample-storage length can have a larger diameter proximal section 106, a lower-friction tube section, a higher-friction tissue engaging second element section, a section absent of or having minimal surface features, a thinner tissue-engaging second element section, or combinations thereof.

The smaller diameter distal section 104 can be about 2.5 cm (1 in) in length. A tissue sample, such as the third tissue sample 11c, as shown, can be in contact with both the helical element 32 and the transport tube 10 while in the smaller diameter distal section 104. The tissue sample 11 can be cored and transported proximally in a direction 105 along the smaller diameter distal section 104 until the tissue sample 11 passes the taper 108.

In the larger diameter proximal section 106, the tissue samples, such as the first and second tissue samples 11a and 11b as shown, may cease to contact the tube 10 and thus cease to rotate with the tube 10. In the larger diameter proximal section 106, the tissue samples 11 may cease to rotate with respect to the helical element 32. As the tool 5 acquires more tissue samples 11, the newly acquired tissue samples 11 can push the previously acquired tissue samples 11 in the larger diameter proximal section 106 further proximally in the direction 105.

The internal face of the smaller diameter distal section 104 may have surface features, such as the internal tissue-engaging features shown in FIG. 9, FIG. 10 and FIG. 22a-g. A non-tapered tube can be used where the tissue-engaging surface features on the internal face of the tube 10 extend a portion of the length of the tube 10 from the distal end 12 of the tube 10, for example about 2.5 cm (1 in). The remainder of the tube 10 can have an internal face or wall absent of surface features (e.g., smooth or low friction). The tissue sample 11 can be urged proximally until the tissue sample 11 reaches the section of the tube 10 absent of the tissue-engaging features. At this section absent of tissue-engaging surface features, the tissue sample 11 may no longer rotate with the tube 10. At this point, the tissue sample 11 may no longer spin, and thus not be urged proximally by the relative rotation of helical element 32 and the tube 10. The section of the tube 10 absent of the tissue-engaging features may be coated with a lubricious material, such as PTFE or Parylene. Thus, although the tissue sample 11 may be in contact with the tube 10, the tube face may not transmit sufficient torque to rotate the tissue sample 11. The helical element 32 may have a low-friction coating for only the distal end, for example for about 2.5 cm (1 in) from the distal end 12. Proximal to the low-friction section, the friction on the helical element 32 may be sufficiently large to prevent the tissue sample 11 from advancing in the direction 105 as the tube 10 spins.

The tool 5 may be configured to be side-cutting, as in FIG. 19a and FIG. 19b. The tool 5 can have a tissue acquisition system. The tissue acquisition system can be the open port 31 at the distal end 12 and the surrounding edge (e.g., as shown and described in FIG. 2, FIG. 3, FIG. 11, FIG. 12, FIG. 13 and elsewhere), a side port (e.g., a window 116) and the internal transport tube 10, or combinations thereof. An external tube 110 can have a closed distal end 114. The closed distal end 114 can be sharpened, for example, for low-resistance insertion and manipulation through the tissue 48. The external tube 110 can have the window 116 proximal to the closed distal end 114. The transport tube 10 may be located concentrically and/or radially internally within the external tube 110, such that the transport tube 10 can move freely with respect to the external tube 110 but have a radial clearance larger than about 0.02 mm (0.001 in), more narrowly larger than about 0.1 mm (0.004 in), yet more narrowly larger than about 0.2 mm (0.008 in), yet more narrowly larger than about 0.3 mm (0.012 in), or yet more narrowly larger than about 0.4 mm (0.015 in). The radial clearance between the internal transport tube 10 and the external tube 110 can be smaller than about 0.4 mm (0.015 in), more narrowly smaller than about 0.3 mm (0.012 in), yet more narrowly smaller than about 0.2 mm (0.008 in), yet more narrowly smaller than about 0.1 mm (0.004 in), or yet more narrowly smaller than about 0.02 mm (0.001 in).

FIG. 19a shows that the transport tube 10 can partially block the window 116. The window 116, may be open prior to sample acquisition, allowing the tissue 48 to enter the tool 5. The tool 5 can be pressed into the targeted portion of tissue 48 so that the tissue sample 11 can enter the external tube 110 via the window 116. A vacuum may be applied to draw the tissue through the window 116. To detach or sever the tissue sample 11, the transport tube 10 and the internal helical element 32 can be advanced forward with respect to the external tube 110 and the tissue sample 11. The transport tube 10 can be rotated or spun while translating with respect to the external tube 110 and the tissue sample 11. The helical element 32 may be rotationally stationary relative to the handle 6. The helical element 32 may be stationary relative to the handle 6.

FIG. 19b shows the tool with the window 116 closed, for example during insertion and/or tissue sample severing (e.g., partoff), and/or tissue sample 11 transport (e.g., translation proximally along the length of the transport tube 10). While the transport tube 10 spins, the tissue sample 11 can be urged proximally, as the tissue sample 11 may engage with the internal helical element 32 and the internal transport tube 10, as described elsewhere herein.

FIG. 20 shows that the transport tube 10 may spin in a direction 9 relative to the helical element 32. The helical element 32, with sharpened distal end 44, may be stationary or spin at a different speed than the transport tube 10 in the same or opposite direction as the transport tube 10. For example, the transport tube 10 can be counter-rotated with respect to the helical element 32 to advance a supplemental device or component (e.g., a tissue marker) or therapy (e.g., liquid or solid pharmacological agents), or combinations thereof, along the transport tube 10 to the target site of tissue 48. The tissue sample 11 can be from about 5 mm (0.2 in.) to about 25 cm (9.8 in.), more narrowly from about 1 cm (0.4 in.) to about 4 cm (1.6 in.), for example about 2 cm (0.8 in.) long. The clearance gap 61 can be the space between the radial inner surface 169 of the external outer element, for example transport tube 10, and the external diameter of the inner internal element, for example helical element 32 or curved stationary element 86.

The inner lumen 139 of the transport tube 10 may have a luminal cross-sectional area, for example about 5 mm$^2$ (0.0078 in$^2$). The tissue engaging second element, such as the helical element 32, can have an inner element cross-sectional area, for example about 0.13 mm$^2$ (0.0002 in$^2$). The inner element cross-sectional area can be less than about 15%, more narrowly less than about 5%, for example about 2.5% of the luminal cross-sectional area.

FIG. 21a, FIG. 21b and FIG. 21c illustrate that the distal end 12 of the tube 10 may be sharpened into a sharp cutting edge. The sharp cutting edge of the distal end 12 may be formed by sharpening the outside diameter of the tube 10, as illustrated in FIG. 21a. The sharp cutting edge of the distal end 12 may be formed by sharpening the inside diameter of the tube 10, as illustrated in FIG. 21c. The sharp cutting edge may be formed by sharpening both the inside and outside diameters of the tube 10. The sharpened cutting edge can have one or more cutting edge angles 136, 138, 140, 142. The cutting edge angles 136, 138, 140 or 142 may be larger than about 5 degrees, more narrowly larger than about 15 degrees, yet more narrowly larger than about 25 degrees, yet more narrowly larger than about 35 degrees, for example about 45 degrees. The cutting edge angles 136, 138, 140, 142 may be smaller than about 45 degrees, more narrowly smaller than about 35 degrees, yet more narrowly smaller than about 25 degrees, yet more narrowly smaller than about 15 degrees, or yet more narrowly smaller than about 5 degrees. The distal end 12 may be comprised of distal angle 138 and proximal angle 140. The distal angle 138 may be larger than the proximal angle 140.

The handle 6 can have the button 22, the motor 34 and the electrical connection 18. A disposable assembly, which can include the tissue-engaging outer element, the tissue-engaging inner element and the collection chamber 26 or a reservoir within the collection chamber 26, or combinations thereof, may then detachably connect mechanically to the reusable handle. The elements of the disposable assembly may be attached or not attached to each other. The disposable assembly may be sterile. The disposable assembly may provide a barrier between the sterile and non-sterile fields, while allowing the operator to actuate the button 22 and the tissue-engaging outer element to engage with the motor 34. After use, the disposable assembly may be disconnected and disposed of in an appropriate fashion. The reusable assembly may be uncleaned, may be wiped down between use, may be sterilized or resterilized, or any combination thereof.

The helical element 32 as disclosed throughout herein may be replaced with any of the tissue-engaging second elements, tissue-engaging inner elements, inner element and vice versa. The transport tube 10 as disclosed throughout herein may be replaced with any of the tissue-engaging first elements, tissue-engaging outer elements, outer element and vice versa.

Figure 22A:
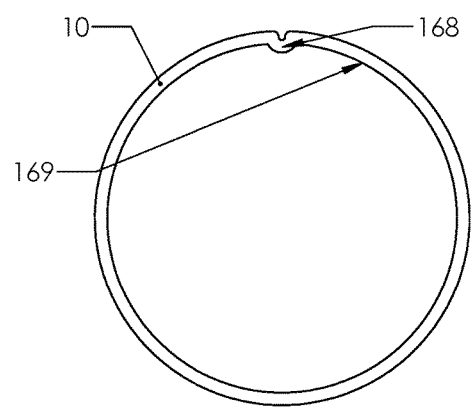

FIG. 22a through FIG. 22g show variations of an internal surface feature on the transport tube 10. The internal surface features, for example detent 168 and/or ribbon 170 and/or overlapping edge 174 and/or traction tab edge 180, can increase torsional traction (e.g., deliver rotational force) between the tissue sample 11 and the transport tube 10. The internal surface feature may not significantly impact traction (e.g., delivering no longitudinal force and providing minimal or no counter force in the longitudinal direction) in the longitudinal direction between the tissue sample 11 and the internal surface feature. Transport tube 10 may have a detent 168, as illustrated in FIG. 22a. Detent 168 may be formed by stamping, rolling, extrusion, or any combination thereof. The inner radial surface 169 at the detent 168 may protrude into the radially inner circular cross-section of the transport tube 10. The detent 168 may thus provide increase torsional traction with the tissue sample 11, when the tissue sample 11 is in the inner lumen. Detent 168 may protrude less than about 0.3 mm (0.012 in) into the radially inner circular cross-section of the transport tube 10, or more narrowly less than about 0.2 mm (0.008 in), for example about 0.1 mm (0.004 in). The detent 168 may extend part or the entire length of the transport tube 10. Multiple detents 168 may be present along the length and/or circumference of the inner radial surface 169.

Figure 22B:
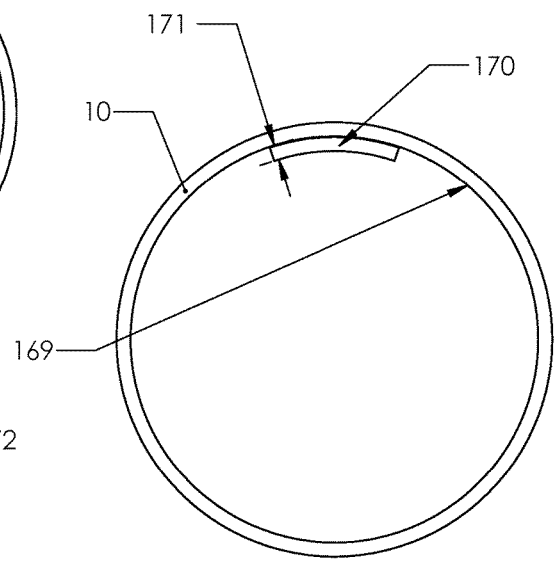

FIG. 22b illustrates that a flat wire 170 may be secured to the inner surface 169 of the transport tube 10. The ribbon 170 may be a section of flat wire or an arc section of a different tube that has been cut. The ribbon 170 may conform to the profile of the inner surface of the transport tube 10. The ribbon 170 may be secured to the transport tube 10 by welding, brazing, glue, or combinations thereof. A ribbon thickness 171 may be less than about 0.3 mm (0.012 in) thick, or more narrowly less than about 0.2 mm (0.008 in) thick, for example about 0.1 mm (0.004 in) thick.

Figure 22C:
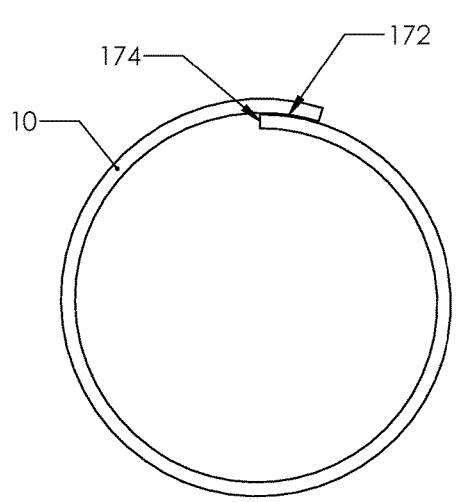

FIG. 22c illustrates that the transport tube 10 may be cut and bent creating an overlapping section 172. The overlapping section 172 may create an overlapping edge 174 on the inner surface of the transport tube 10. The overlapping section 172 may be secured by welding, brazing, gluing, friction, interlocking tabs, or any combination thereof. The overlapping edge 174 may provide high friction or traction against a tissue sample in the inner lumen when the tube 10 is rotated in a first rotational direction with respect to the longitudinal axis, and low friction or traction against the tissue sample when the transport tube 10 is rotated in a second direction, opposite the first direction, with respect to the longitudinal axis. For example, the overlapping edge may transfer torque to the tissue sample 11 when the transport tube 10 is rotated clockwise, but not when the transport tube 10 is rotated counter-clockwise.

Figure 22D:
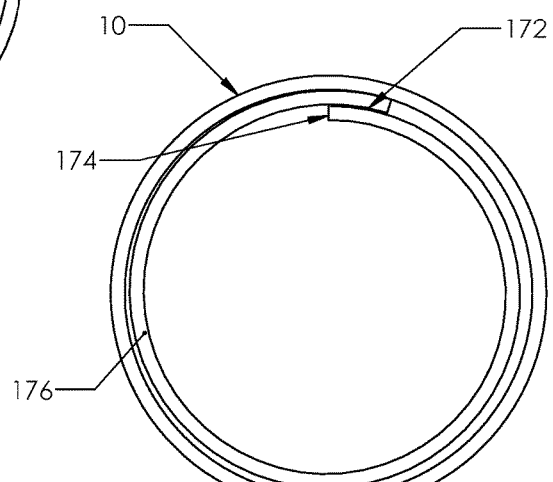

FIG. 22d illustrates that an overlapping tube 176 may be pressed into the transport tube 10. The transport tube 10 may be of an appropriate stiffness to maintain a circular cross-section while constraining the overlapping section 172. For example, the overlapping section 172 may be formed by radially the overlapping tube 176. This overlapping tube 176 may exert a radial force in the opposite direction to counter the compression. This force may secure the overlapping tube 176 in the transport tube 10, for example with friction. The transport tube 10 may be stiff enough to maintain a circular cross-section while exposed to this force.

FIG. 22e illustrates that the distal end of the overlapping tube 176 may be proximal to the terminal distal end 12 of the transport tube 10. The overlapping tube 176 may have a sharp distal edge similar to the terminal distal end 12, for example as illustrated in FIGS. 21a through 21c. The distal end of the overlapping tube 176 may extend past or be flush with the terminal distal end 12. The distance between the distal end of overlapping tube 176 and distal end 12 may be larger than about 0.5 mm (0.02 in), yet more narrowly larger than about 1 mm (0.04 in), yet more narrowly larger than about 1.5 mm (0.06 in), yet more narrowly larger than about 2 mm (0.08 in), yet more narrowly larger than about 2.5 mm (0.10 in), yet more narrowly larger than about 3 mm (0.12 in), yet more narrowly larger than about 3.5 mm (0.14 in), yet more narrowly larger than about 4 mm (0.16 in), yet more narrowly larger than about 4.5 mm (0.18 in), yet more narrowly larger than about 5 mm (0.20 in), yet more narrowly larger than about 6 mm (0.24 in), yet more narrowly larger than about 7 mm (0.28 in), yet more narrowly larger than about 10 mm (0.39 in). The distance between the distal end of overlapping tube 176 and distal end 12 may be less than about 10 mm (0.39 in), yet more narrowly less than about 7 mm (0.28 in), yet more narrowly less than about 6 mm (0.24 in), yet more narrowly less than about 5 mm (0.20 in), yet more narrowly less than about 4.5 mm (0.18 in), yet more narrowly less than about 4 mm (0.16 in), yet more narrowly less than about 3.5 mm (0.14 in), yet more narrowly less than about 3 mm (0.12 in), yet more narrowly less than about 2.5 mm (0.10 in), yet more narrowly less than about 2 mm (0.08 in), yet more narrowly less than about 1.5 mm (0.06 in), yet more narrowly less than about 1 mm (0.04 in), yet more narrowly less than about 0.5 mm (0.02 in).

FIG. 22f illustrates that a traction tab 178 may be formed on the side of the transport tube 10. The transport tube 10 may have one or more traction tabs 178. The traction tab 178 may extend the entire length of the transport tube 10 or for a section of the transport tube 10. A long traction tab 178 may decrease the stiffness of the transport tube 10. Multiple traction tabs 178 may provide sufficient traction without significantly impacting the stiffness of the transport tube 10. If multiple tabs are formed, they may be overlapped, as illustrated. For example, traction tabs 178a and 178b may overlap.

FIG. 22g illustrates that the traction tab 178 can be a terminal angular end of a length of a longitudinally cut transport tube 10. The traction tab 178 can be radially inside the opposite terminal angular end of the transport tube 10. The traction tab 178 can press radially outward against the radially inner surface of the opposite terminal angular end of the transport tube 10. The traction tab 178 can be bent to hold its shape so that it does not press radially outward against the radially inner surface of the opposite terminal angular end of the transport tube 10. The Traction tab 178 can have a traction tab edge 180. The traction tab edge 180 may create an elongated ridge for transmitting torque to tissue sample 11. Traction tab 178 can be formed by stamping the metal (e.g., shearing), laser cutting, machining, wire EDM, chemical etching, or any combination thereof.

Figure 23A:
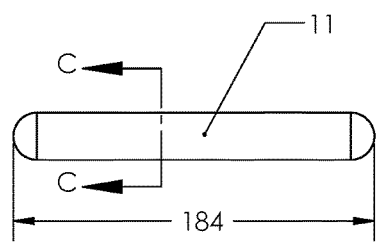
FIG. 23a and FIG. 23b illustrate a tissue sample.

FIG. 23a illustrates the tissue sample 11 can have a continuous elongated configuration. The tissue sample 11 can have a tissue sample length 184 from about 0.5 cm (0.2 in) to about 4 cm (1.6 in), more narrowly from about 1 cm (0.4 in) to about 3 cm (1.2 in), for example about 2 cm (0.8 in).

Figure 23B:
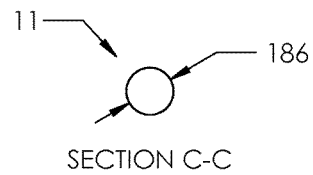

FIG. 23b illustrates that the tissue sample 11 can have a circular cross-section along all or part of the length of the tissue sample 11. The cross-section of the tissue sample 11 can vary along the length of the tissue sample 11, for example from anatomical variations along the length of the tissue sample 11. The cross-section of the tissue sample 11 can have a continuous profile (i.e., the cross-section can have no holes or deformations entirely within the perimeter of the cross-section). The cross-section of the tissue sample 11 can be simply connected or 1-connected. A space can be simply connected or 1-connected if it is path-connected and every path between two points can be continuously transformed, staying within the space, into any other path while preserving the two endpoints in question.

The tissue sample can have a tissue sample diameter 186 from about 1 mm (0.04 in) to about 6 mm (0.24 in), more narrowly from about 2 mm (0.08 in) to about 4 mm (0.16 in), for example about 3 mm (0.12 in).

Figure 24A:
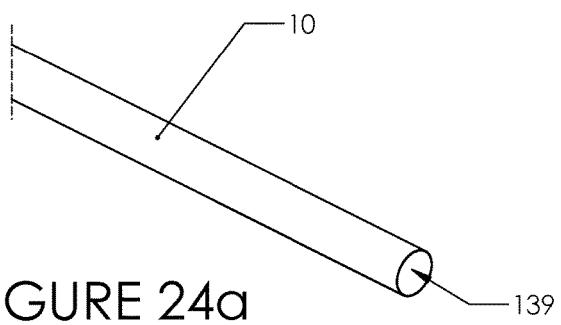
FIG. 24a is an isometric view of the distal end of the transport tube.

FIG. 24a illustrates that the inner lumen 139 can be the volume bounded or defined by the inner perimeter or inner diameter or radial inner surface of the external or outer element. For example, the inner lumen 139 can be the volume bounded by transport tube 10 and any surface features, such as an overlapping tube and/or ribbon and/or rib and/or spiral rib, located on the radial inner surface of the transport tube 10.

Figure 24B:
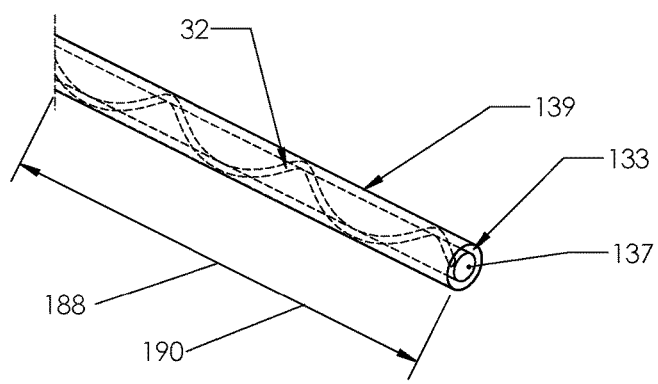
FIG. 24b is a transparent isometric view of the distal end of the inner lumen.

FIG. 24b illustrates that the inner lumen 139 can have or contain a transport channel 133 and the tissue-engaging inner element (e.g., helical element 32). The inner diameter of the inner element can define a transport cylinder 137 within the transport channel 133. During use, the tissue sample 11 can transport along the transport channel 133. The transport cylinder 137 can be an uninterrupted, open volume. The transverse cross-section of the transport cylinder 137 can be a continuous profile (i.e., the cross-section can have no holes or deformations entirely within the perimeter of the cross-section). The transverse cross-section of the transport cylinder 137 can be simply connected.

The transport channel 139 can have a transport channel length 188. The transport cylinder 137 can have a transport cylinder length 190. The transport channel length 188 can be equal to or greater than the transport cylinder length 190. The transport cylinder length 190 can be smaller than, equal to or greater than an external element length 39. The transport channel 133 and transport cylinder 137 can extend along part or all of the length of the inner lumen 139.

The axis 8 of the transport tube 10 can be radially inside of the transport cylinder 137. The transport channel 133 and/or the transport cylinder 137 can have a diameter from about 1 mm (0.04 in) to about 6 mm (0.24 in), more narrowly from about 2 mm (0.08 in) to about 4 mm (0.16 in), for example about 3 mm (0.12 in).

The transport tube 10 can have surface features, such as the detent 168, the ribbon 170, the overlapping edge 174 and the traction tab edge 180 or combinations thereof. An elongated ridge parallel with a longitudinal axis may be a surface feature, for example the detent 168, the ribbon 170, the overlapping edge 174, the traction tab edge 180 or any combination thereof.

It is apparent to one skilled in the art that various changes and modifications can be made to this disclosure, and equivalents employed, or combinations of any of the disclosed elements, characteristics, features, devices, tools, steps, or methods without departing from the spirit and scope of the invention. Any of the disclosed elements, characteristics, features, devices, tools, steps, or methods can be present as a singular or as a plurality regardless of whether the elements, characteristics, features, devices, steps, or methods are explicitly disclosed herein as being singular or as a plurality. Elements shown with any variation are exemplary for the specific variation and can be used on other variation within this disclosure.

I claim:

1. A tool for acquiring a tissue at a tissue site comprising:
    a tissue-engaging outer element comprising a substantially tubular structure having a lumenal cross-sectional area; and
    a tissue-engaging inner element located at least partially within the tissue-engaging outer element; wherein at least one of the tissue-engaging outer element and the tissue-engaging inner element comprises a helical feature,
    wherein the tool is configured such that relative rotation between the tissue-engaging outer element and the tissue-engaging inner element urges the tissue in an axial direction, and wherein the tissue-engaging inner element occupies less than 15% of the lumenal cross-sectional area,
    wherein the tissue-engaging outer element has an open first end and an open second end,
    wherein the tissue-engaging outer element is configured to receive the tissue in the first end and deposit the tissue out of the second end,
    wherein the second end is configured to be open to atmospheric pressure, and
    wherein the relative rotation between the tissue-engaging outer element and the tissue-engaging inner element transports the tissue from the first end out of the second end.

2. The tool of claim 1 wherein the tissue-engaging inner element occupies less than 5% of the lumenal cross-sectional area.

3. The tool of claim 1 wherein the tissue-engaging inner element occupies less than 2.5% of the lumenal cross-sectional area.

4. The tool of claim 1, wherein a terminal distal end of the tissue-engaging outer element is sharpened and configured to core the tissue from the tissue-site when the tissue-engaging outer element rotates with respect to the tissue site; and wherein the tissue-engaging inner element comprises a coiled wire having a circular cross-section.

5. The tool of claim 1, wherein the tissue-engaging outer element has a tissue-contacting first surface and the tissue-engaging inner element has a tissue-contacting second surface, and wherein at least one of the tissue-contacting first surface and the tissue-contacting second surface comprise a surface feature, and
    wherein the surface feature comprises at least one of spiral ribs, helical ribs, axial ribs, rifling, knurling, ridges, spines, barbs, coatings, texturing, an overlapping tube, overlapping tubes, a ribbon, and ribbons.

6. The tool of claim 1, wherein the tissue-engaging inner element is configured to transport a supplemental device or therapy at least one of distally and proximally along the tissue engaging outer element.

7. The tool of claim 1, wherein the helical feature extends from a distal end to a proximal end of the tissue-engaging outer element or the tissue-engaging inner element.

* * * * *